US012330181B2

(12) United States Patent
Morihisa

(10) Patent No.: US 12,330,181 B2
(45) Date of Patent: Jun. 17, 2025

(54) SPRAYING APPARATUS

(71) Applicant: K.K. KUKAN JOKIN, Tokyo (JP)

(72) Inventor: Yasuhiko Morihisa, Tokyo (JP)

(73) Assignee: K.K. KUKAN JOKIN, Tokyo (JP)

( * ) Notice: Subject to any disclaimer, the term of this patent is extended or adjusted under 35 U.S.C. 154(b) by 455 days.

(21) Appl. No.: 17/911,408

(22) PCT Filed: Mar. 4, 2021

(86) PCT No.: PCT/JP2021/008361
§ 371 (c)(1),
(2) Date: Sep. 13, 2022

(87) PCT Pub. No.: WO2021/182271
PCT Pub. Date: Sep. 16, 2021

(65) Prior Publication Data
US 2023/0107432 A1 Apr. 6, 2023

(30) Foreign Application Priority Data
Mar. 13, 2020 (JP) ................. 2020-043628

(51) Int. Cl.
B05B 7/24 (2006.01)
A61L 2/22 (2006.01)
(Continued)

(52) U.S. Cl.
CPC .............. B05B 7/2491 (2013.01); A61L 2/22 (2013.01); A61L 2/26 (2013.01); B05B 7/0012 (2013.01);
(Continued)

(58) Field of Classification Search
CPC . B05B 7/2491; B05B 7/0012; B05B 17/0615; A61L 2/22; A61L 2/26; A61L 2202/15; A61L 2202/25
(Continued)

(56) References Cited

U.S. PATENT DOCUMENTS

2005/0017092 A1* 1/2005 Kinoshita ............. B05B 7/0012
239/428
2013/0026250 A1* 1/2013 Burt .................... B05B 17/0615
239/302

FOREIGN PATENT DOCUMENTS

JP S60-50728 U 4/1985
JP H08-309248 A 11/1996
(Continued)

Primary Examiner — Steven J Ganey
(74) Attorney, Agent, or Firm — j-pat U.S. Patent Legal Services; James Judge

(57) ABSTRACT

Spraying apparatus enabling large-volume generation of particles minute to a Brownian-motion engendering level. The spraying apparatus includes a top-paneled atomization tank having blow and send-out ports in the top panel, an atomizing device inside the atomization tank, a blower for blowing air through the blow port into the tank, and first and second baffle plates, respective connection parts of which are connected to the inner side of the top panel. Respective edge parts of the first and second baffle plates lie at predetermined spacings from widthwise-opposing interior surfaces of the atomization tank. The blow port is situated to the one tank widthwise interior-surface side of where the first baffle-plate connection part is connected to the top panel, while the send-out port is situated to the other tank widthwise interior-surface side of where the second baffle-plate connection part is connected.

4 Claims, 20 Drawing Sheets

(51) Int. Cl.
 _A61L 2/26_ (2006.01)
 _B05B 7/00_ (2006.01)
 _B05B 17/06_ (2006.01)

(52) U.S. Cl.
 CPC ....... _B05B 17/0615_ (2013.01); _A61L 2202/15_ (2013.01); _A61L 2202/25_ (2013.01)

(58) Field of Classification Search
 USPC .......................................... 239/102.1, 102.2
 See application file for complete search history.

(56) References Cited

FOREIGN PATENT DOCUMENTS

| | | |
|---|---|---|
| JP | 2004-216221 A | 8/2004 |
| JP | 3224953 U | 1/2020 |

\* cited by examiner

SPRAYING APPARATUS

TECHNICAL FIELD

The present invention relates to technology for generating fine particles in a spraying device that sprays liquid into a space.

BACKGROUND ART

Various spraying devices that atomize and spray into a space water or aqueous solutions that exhibit predetermined effects have been developed.

In spraying devices of this kind, in order to uniformly and wide-rangingly diffuse fine particles inside a space, it is necessary to stably generate fine particles having a desired particle size—in particular, a particle size tiny to a level at which the fine particles can give rise to Brownian motion within air.

As an example of this sort of spraying device, there is the instance in which, e.g., in a broad space such as an elderly-facility assembly hall, or livestock shelter such as a cow-shed, piggery, or poultry farm, the need arises to spray a large volume of a liquid formulation having a disinfecting action. In such instances, it is undesirable that the particle diameters be large, because the particles will fall to the floor or ground before reaching every nook and cranny of the space, and at the same time dampen the floor, walls, and skin, becoming the cause of slipping, of mold and mildew, and of colds. Therefore, in order that the particles float within the air for a long time such that the sterilizing effectiveness is demonstrated, it is necessary to generate fine particles having particle diameters tiny to a level that can give rise to Brownian motion.

In general, in order to atomize and spray a liquid, in an atomizing unit in which water or an aqueous solution is stored, technology is adopted in which a liquid column generated utilizing a vibrator such as an ultrasonic vibrator is impacted on a separator and separated into large liquid droplets and small mist droplets, and a conveyance medium supplied from a blower or the like is utilized to convey and diffuse into the air the mist droplets alone. (Patent Document 1, Patent Document 2) Precedent Technical Literature Patent Document(s)

Patent document 1: JP H8-309248 A
Patent Document 2: JP S60-50728 U

SUMMARY OF INVENTION

Issues Invention is to Address

The technology disclosed in Patent Document 1 and Patent Document 2 affords a spray apparatus capable of selectively spraying mist droplets separated from liquid droplets. Nevertheless, with the technology disclosed in Patent Documents 1 and 2, because air is directly supplied to the region where the liquid column collides on the separator, due to the air the flow is disturbed, such that particles of relatively large particle diameter also get swept into and are conveyed on the air. Consequently, the particle diameter of fine particles conveyed on the air and sprayed is on the order of 10 μm, encumbering the generating of fine particles (particle size of about 0.1 to 2 μm) that are tiny to a level that can give rise to Brownian motion.

What is more, in order to evenly spread fine particles over a broad space, it is necessary to supply a large volume of conveyance air for conveying the fine particles, meaning that in such cases not only fine particles of tiny diameter but also particles whose diameter is large are conveyed, making difficult the conveying of only fine particles that are tiny to a level that can give rise to Brownian motion.

Generating/conveying only tiny fine particles necessitates controlling with high precision the voltage applied to the vibrator and the rpm of the delivery machine at the same time, which without specialized knowledge is challenging.

An object of the present invention, brought about taking these sorts of issues into consideration, is to make available a spraying apparatus capable of generating a large volume of fine particles having particle diameters minute to a level that stably can give rise to Brownian motion, even without complex control employing expensive control devices.

Means for Resolving Issues

The inventors of the present invention, finding that fine particles having particle diameters minute to a level that can give rise to Brownian motion can be generated at large volume by arranging a blower, ultrasonic vibrators, baffle plates, and a separator in specified positions within an atomizing unit, arrived at the present invention.

The present invention makes available the following sort of resolution means.

The invention involving a first characteristic affords a spraying apparatus provided with: an atomization tank having a predetermined width, enabled for storing a liquid formulation; an atomizing device being ultrasound vibrating elements plurally arranged widthwise in the atomization tank interior, for atomizing the liquid formulation to generate fine particles; a blower furnished with a blowing element enabled for maintaining predetermined rpm, for blasting into the atomization tank interior, through a blow port provided in the atomization tank, conveyance air that is for conveying the fine particles of the liquid formulation; a send-out port, provided in the atomization tank, through which the fine particles are sent out together with the conveyance air; a first baffle plate arranged so as to receive liquid columns of the liquid formulation, generated by an ultrasound vibration element that among said ultrasound vibration elements is arranged along one widthwise end thereof; a second baffle plate arranged so as to receive liquid columns of the liquid formulation, generated by an ultrasound vibration element that among said ultrasound vibration elements is arranged along the other widthwise end thereof; wherein the first baffle plate is arranged inclined laterally or diagonally downward, directed toward the one widthwise end of the atomization tank, and is furnished with a first edge piece disposed in the atomization tank spaced apart at a predetermined spacing from an inner face along the one widthwise end, and with a first connection piece, connected to an inner side of a top panel of the atomization tank; the blow port is arranged along the top panel of the atomization tank more to the one widthwise end of the atomization tank than is the first connection piece, and more to the other widthwise end of the atomization tank than is the first edge piece; the second baffle plate is arranged inclined laterally or diagonally downward, directed toward the other widthwise end of the atomization tank, and is furnished with a second edge piece disposed in the atomization tank spaced apart at a predetermined spacing from an inner face along the other widthwise end, and with a second connection piece, connected to the inner side of the top panel of the atomization tank; and the send-out port is arranged more toward the other widthwise end of the atomization tank than is the second connection piece.

Further, the invention involving a second characteristic affords a spraying apparatus provided with: an atomization tank having a predetermined width, enabled for storing a liquid formulation; an atomizing device being ultrasound vibrating elements plurally arranged widthwise in the atomization tank interior, for atomizing the liquid formulation to generate fine particles; a blower furnished with a blowing element enabled for maintaining predetermined rpm, for blasting into the atomization tank interior, through a blow port provided in the atomization tank, conveyance air that is for conveying the fine particles of the liquid formulation; a send-out port, provided in the atomization tank, through which the fine particles are sent out together with the conveyance air; a first baffle plate arranged so as to receive liquid columns of the liquid formulation, generated by an ultrasound vibration element that among said ultrasound vibration elements is arranged along one widthwise end thereof; a second baffle plate arranged so as to receive liquid columns of the liquid formulation, generated by an ultrasound vibration element that among said ultrasound vibration elements is arranged along the other widthwise end thereof; wherein the first baffle plate is arranged inclined laterally or diagonally downward, directed toward the one widthwise end of the atomization tank, and is furnished with a first edge piece disposed in the atomization tank spaced apart at a predetermined spacing from an inner face along the one widthwise end, and with a first connection piece, connected to an inner side of a top panel of the atomization tank; the blow port is arranged in a lateral surface along the one widthwise end of the atomization tank, upward of the first edge piece; the second baffle plate is arranged inclined laterally or diagonally downward, directed toward the other widthwise end of the atomization tank, and is furnished with a second edge piece disposed in the atomization tank spaced apart at a predetermined spacing from an inner face along the other widthwise end, and with a second connection piece, connected to the inner side of the top panel of the atomization tank; and the send-out port is arranged more toward the other widthwise end of the atomization tank than is the second connection piece.

According to the invention involving the first or second characteristic, because it has a configuration in which the first baffle plate is arranged at one widthwise end of the atomization tank, inclined laterally or obliquely downward, directed toward the one widthwise end of the atomization tank, and is furnished with a first edge piece disposed in the atomization tank spaced apart at a predetermined spacing from the inner face at one widthwise end, and a first connection piece connected to the inner face of the top panel of the atomization tank, and a configuration in which the air blow port serving as an inlet for conveyance air is arranged along the top panel of the atomization tank more to the one widthwise end of the atomization tank than is the first connection piece and more to the other widthwise end than is the first edge piece, and further, in a lateral surface along the one widthwise end of the atomization tank, upward of the first edge piece, almost the entire amount of conveyance air blown in through the air blow port follows the orientation in which the first baffle plate is arranged, forming a flow directed toward the one widthwise end, with conveyance air flowing in the one widthwise-end orientation passing through a gap created between the first edge piece and the lateral surface of the atomization tank.

Then, because the send-out port is provided more toward the other widthwise end of the atomization tank than is the second connection piece, which is a connection piece between the second baffle plate provided at the other widthwise end and the atomization tank, conveyance air that has passed through the spacing created between the first edge piece and the atomization tank lateral surface directionally converts into a flow in the orientation of the other widthwise end, and going past the second baffle plate and flowing toward the other widthwise end. In this way, by conveyance air supplied through the blow port initially flowing in the direction of the one widthwise end of the atomization tank, next passing through the gap, and then directionally converting toward the other widthwise end, over the entire atomization tank a large swirling flow straddling the first baffle plate and the second baffle plate is created.

Then, in passing along the underside of the first baffle plate and the second baffle plate, tiny particles alone are conveyed; in that situation, because a swirling flow over the entire atomization tank is created, combined with the effects of centrifugation due to the swirling flow, fine particles having particle diameters tiny to a level that gives rise to Brownian motion can be alone conveyed in large quantities.

Further, when conveyance air passes through the gap between the first edge piece and the lateral surface of the atomization tank, a one-time compressed flow occurs, and because the conveyance air expands after passing through the gap, negative pressure occurs in the post-gap-passing region—namely, in the vicinity of the undersurface of the first baffle plate, which receives the liquid column of the liquid formulation. In the negative pressure region, the pressure of the conveyance air drops still further, and therefore particles other than fine particles that are of extraordinarily tiny particle diameter cannot be conveyed, meaning they fall to the liquid surface below. As a result, fine particles of a particle diameter tiny to a level that can give rise to Brownian motion can alone be conveyed toward the send-out port by the conveyance air.

That is, the present invention enables, even without complex control, the generating of a large volume of fine particles having particle diameters minute to a level that stably can give rise to Brownian motion.

Effect of the Invention

According to the present invention, a spraying apparatus that, even for persons for whom the job is unfamiliar, is capable of generating a large volume of fine particles having particle diameters minute to a level that stably can give rise to Brownian motion, even without complex control employing expensive control devices, may be made available.

MODE(S) FOR IMPLEMENTING INVENTION

Hereinafter, modes for implementing the present invention will be described with reference to the drawings. It should be noted that this is just an example, and the technical scope of the present invention is not limited to this.

Overall Configuration of Spray Apparatus

Figure 1A:
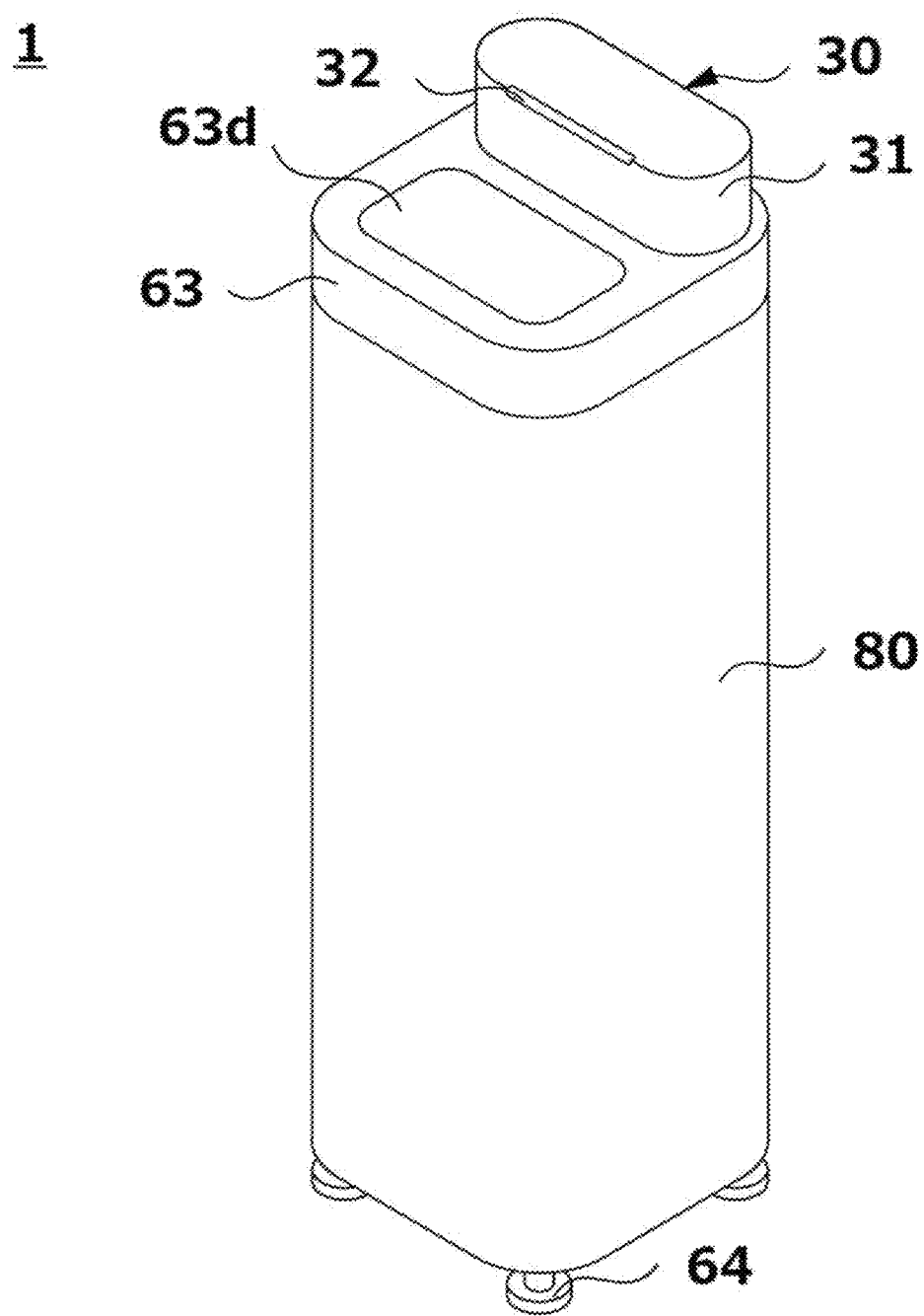
FIG. 1A is a perspective view of a spraying apparatus 1 involving a core embodying mode.
Figure 1B:
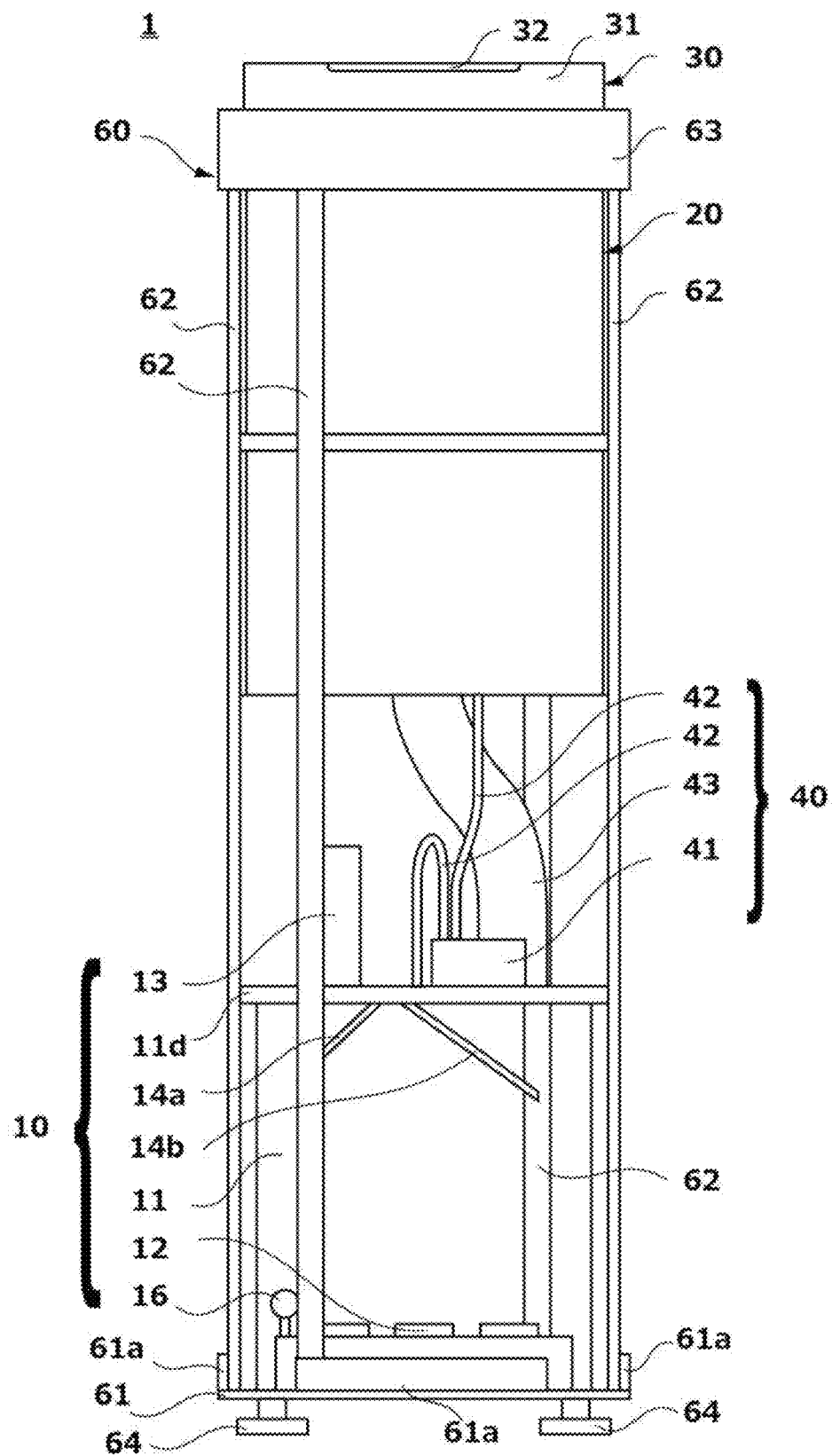
FIG. 1B is an elevational view of the spraying apparatus 1 involving the core embodying mode, with its cover member 80 having been removed.
Figure 1C:
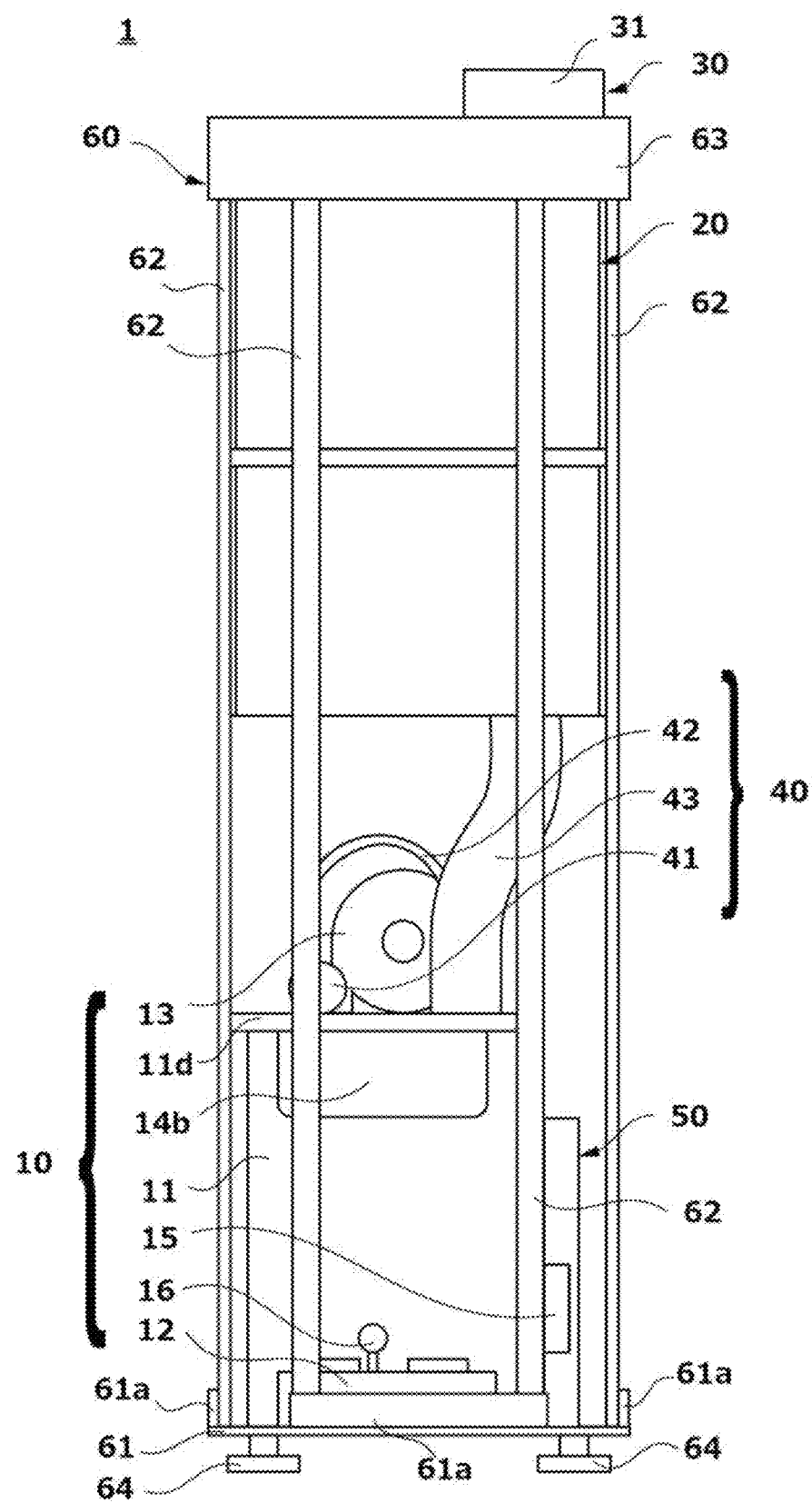
FIG. 1C is a right lateral side view of the spraying apparatus 1 involving the core embodying mode, with its cover member 80 having been removed.
Figure 1D:
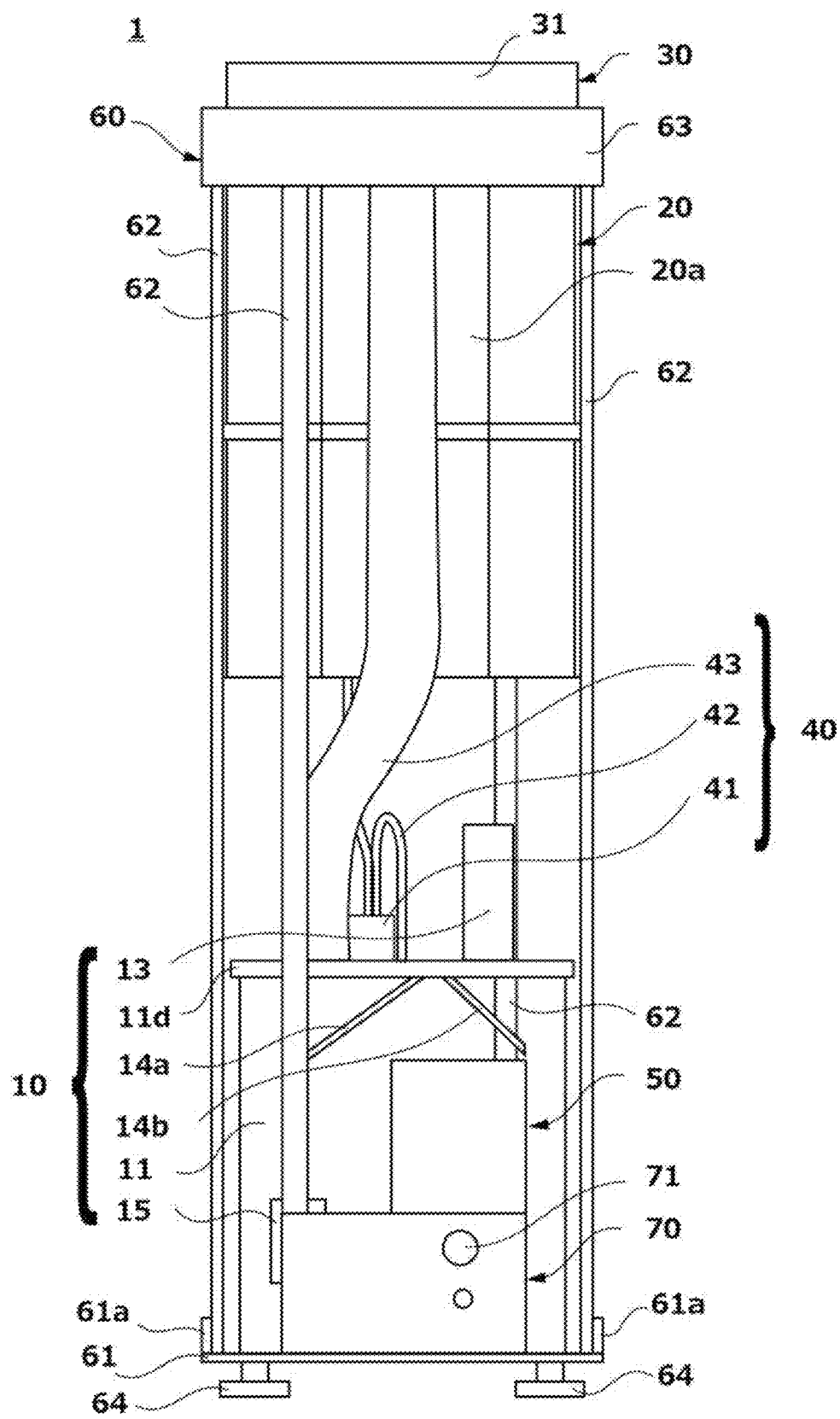
FIG. 1D is a rear side view of the spraying apparatus 1 involving the core embodying mode, with its cover member 80 having been removed.

With reference to FIG. 1A-1D, the overall configuration of spraying device 1 according to the present embodying mode will be described. FIG. 1A shows a perspective view, FIG. 1B shows a front view with a cover member 80 removed, FIG. 1C shows a right-side view with the cover member 80 removed, and FIG. 1D shows a rear view with the cover member 80 removed. It should be noted that in FIG. 1B, illustration of a liquid level sensor 15, a control unit 50, and a power supply unit 70 is omitted, and in FIG. 1C, illustration of the power supply unit 70 is omitted.

As illustrated in FIGS. 1A to 1D, the spraying apparatus 1 of the present embodying mode is constituted by: an atomizing unit 10 that atomizes a liquid formulation to generate and convey fine particles; a tank unit 20 that stores a liquid formulation to be supplied to the atomizing unit; a spouting unit 30 that spouts the fine particles generated by the atomizing unit 10; a supply unit 40 that sends out the fine particles generated in the atomizing unit 10 and supplies the liquid formulation to the atomizing unit 10; a control unit 50 that controls instruments; an mounting unit 60 that fixes each unit together; a power supply unit 70 that supplies power to each instrument; and a cover member 80 that covers each unit.

In addition, in the present embodying mode, it is assumed that a chlorous acid aqueous solution having a sterilizing effect is used as the liquid formulation, and the spraying apparatus 1 is used as a sterilizing device that kills viruses and bacteria floating in the air.

Configuration of Atomizing Unit 10

Figure 2A:
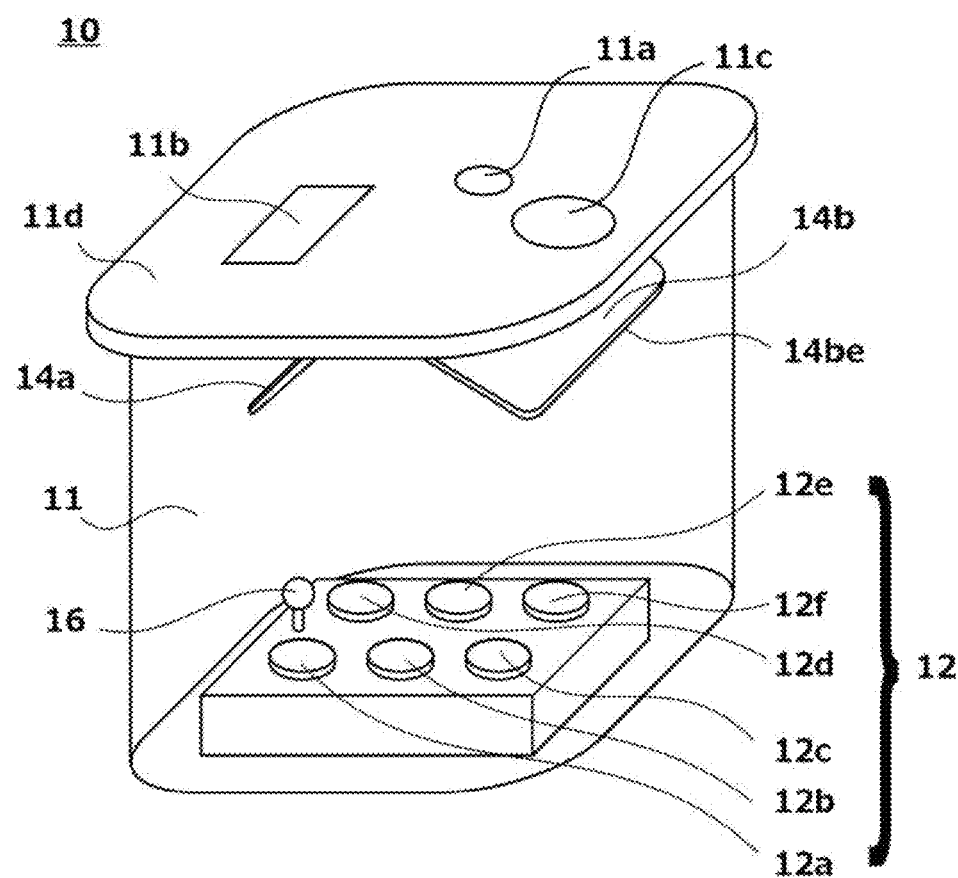
FIG. 2A is a partially enlarged perspective view of an atomization unit 10 involving the core embodying mode.

With reference to FIGS. 1 and 2, the atomizing unit 10 according to the present embodying mode will be described. FIG. 2A shows a partially-enlarged perspective view of the atomizing unit 10, and FIG. 2B is a schematic diagram illustrating how the atomizing unit 10 is used.

As illustrated in FIG. 2A, the atomizing unit 10 includes an atomization tank 11 having a predetermined width, enabled for storing a liquid formulation; an atomizing device 12 being ultrasonic vibrators 12*a*, 12*b*, 12*c* . . . plurally arranged widthwise and depthwise in the atomization tank 11 interior, for atomizing the liquid formulation to produce fine particles; a blower 13 furnished with a blowing element, not illustrated, enabled for maintaining predetermined rpm, for blasting into the atomization tank 11 interior, through a blow port 11*b* provided in the atomization tank 11, conveyance air that is for conveying the fine particles of the liquid formulation; two baffle plates 14*a* and 14*b* arranged so as to receive liquid columns of the liquid formulation, produced by the ultrasonic vibrators 12*a*, 12*b*, 12*c* . . . ; and a liquid level sensor 15 for detecting a liquid level in the atomization tank 11.

The atomization tank 11 is for storing and atomizing the liquid formulation supplied from the tank unit 20, and has a substantially rectangular parallelepiped shape having a predetermined width. In the top panel 11*d* of the atomization tank 11, a supply port 11*a* is formed; through the supply port 11*a*, the liquid formulation supplied from the tank unit 20 through the liquid-formulation supply pump 41 of the later-described supply unit 40 flows into the atomization tank 11 interior. In addition, in the top panel 11*d* of the atomization tank 11, a blow port 11*b* is formed; through the blow port 11*b*, the conveyance air from the blower 13 flows into the atomization tank 11 interior. Furthermore, in the top panel 11*d* of the atomization tank 11, a send-out port 11*c* is formed; through the send-out port 11*c*, the fine particles atomized in the atomization tank 11 is sent out along with the conveyance air. The atomization tank 11 is fixed to a lower-part base 61 of the later-described mounting unit 60 by known means such as screw-fastening. In this situation, the atomization tank 11 is arranged inside the region defined by six columnar members 62 of the mounting unit 60. The atomization tank 11 is made of polyethylene terephthalate (PET). In addition, in the present embodying mode, the top panel 11*d* of the atomization tank 11 is formed of a top panel piece attached to the main body of the atomization tank 11.

The atomizing device 12, being a device equipped with a plurality of ultrasonic vibrators 12*a*, 12*b*, 12*c* . . . arranged at the bottom inside the atomization tank 11, is operated by the power supplied from the power supply unit 70 to emit ultrasonic waves. The atomizing device 12 according to the present embodying mode, in which ultrasonic vibrators 12*a*, 12*b*, 12*c*, 12*d*, 12*e*, and 12*f* are arranged in a plane in two rows along the depth and in three rows along the width of the atomization tank 11, atomizes the liquid formulation wide-rangingly in the atomization tank 11 wide-rangingly to produce fine particles. When the atomizing device 12 is operated, from the liquid surface, for each of the arranged ultrasonic vibrators 12*a*, 12*b*, 12*c* . . . , a liquid column is produced upward from each of the ultrasonic vibrators 12*a*, 12*b*, 12*c* . . . .

The blower 13, furnished with a blowing element not illustrated whose rpm can be controlled according to a signal from the control unit 50, is for supplying conveyance air for conveying the atomized liquid formulation through the blow port 11b into the atomization tank 11 interior, and a blast port, not illustrated, for blasting the conveyance air is connected to the blow port 11b of the atomization tank 11, arranged so as to be able to blow air downward. In the present embodying mode, the blower 13, driven by power supplied from the power supply unit 70, is rpm-controlled by changing the applied voltage according to a signal from the control unit 50.

Next, the two baffle plates 14a and 14b will be described. The baffle plates 14a and 14b are flat pieces formed of stainless steel, and their basic function is to separate the liquid droplets produced by the ultrasonic vibration of the atomizing device 12 into large liquid droplets and tiny fine particles. That is, when a liquid column is produced above each of the ultrasonic vibrators 12*a*, 12*b*, 12*c* . . . , liquid droplets of large particle diameter contained in the liquid column collide on the baffle plates 14*a* and 14*b*, and flow downward and then back to the liquid layer stored in the atomization tank 11. On the other hand, mist droplets of small particle diameter contained in the liquid column float in the vicinity of the baffle plates 14*a* and 14*b*, and are conveyed to the send-out port 11*c* by the conveyance air supplied by the blower 13. In this manner, by the action of the baffle plates 14*a* and 14*b*, the liquid droplets of large particle diameter and the mist droplets of small particle diameter produced by ultrasonic vibration can be separated.

In addition to this basic function, the baffle plates 14*a* and 14*b* according to the present embodying mode are arranged as follows so as to exhibit further function described below.

The baffle plate 14*a* according to the present embodying mode (first baffle plate in the present invention) is arranged below the blow port 11*b* and above the ultrasonic vibrators 12*a* and 12*d* arranged along one widthwise end of the atomization tank 11 among the ultrasonic vibrators.

In addition, the baffle plate 14*a* is arranged to incline downward toward the one widthwise end of the atomization tank 11, in such a manner that one end has a connection piece 14*ac* (first connection piece in the present invention) connected to the top panel 11*d* of the atomization tank 11, and the other end has an edge piece 14*ae* (first edge piece in the present invention) arranged spaced apart at a predetermined spacing from the lateral surface along one widthwise end of the atomization tank 11.

The baffle plate 14*b* (second baffle plate in the present invention) is arranged below the supply port 11*a* and the send-out port 11*c* and above the ultrasonic vibrators 12*c* and 12*f* arranged along the other widthwise end of the atomization tank 11 among the ultrasonic vibrators.

In addition, the baffle plate 14*b* is arranged inclined diagonally downward, toward the opposite side from the baffle plate 14*a*, that is, toward the other widthwise end of the atomization tank 11, in such a manner that one end has a connection piece 14*bc* (second connection piece in the present invention) connected to the top panel of the atomization tank 11, and the other end has an edge piece 14*be* (second edge piece of the present invention) arranged spaced apart at a predetermined spacing from the lateral surface along the other widthwise end of the atomization tank 11, that is, on the side opposite from the side where the baffle plate 14*a* is arranged.

In other words, the end part of the baffle plate 14*a* is arranged spaced apart at a predetermined spacing from the lateral surface along one widthwise end of the atomization tank 11, while the end part of the baffle plate 14*b* is arranged spaced apart at a predetermined spacing from the lateral surface along the other widthwise end of the atomization tank 11.

The blow port 11*b* is provided to one widthwise end of the connection piece 14*ac* of the baffle plate 14*a*, and the send-out port 11*c* is provided to the other widthwise end of the connection piece 14*bc* of the baffle plate 14*b*.

The liquid-level sensor 15 is for detecting liquid level in the liquid formulation stored in the atomization tank 11 interior, and in the present embodying mode, a float sensor arranged in the external part of the atomization tank 11 is employed. In this case, the atomization tank 11 is provided with a flow through-hole, not illustrated, at an appropriate height, and the liquid formulation flows into the liquid-level sensor 15 via the flow through-hole. Since the atomization tank 11 and the liquid-level sensor 15 connected via the flow through-hole are under the same pressure, the liquid level in the liquid-level sensor 15 and the liquid level in the atomization tank 11 have the same value. In this manner, the liquid level in the atomization tank 11 is detected by the external liquid-level sensor 15, but the sensor is not limited to this as long as the liquid level can be measured. The liquid-level sensor 15 in the present embodying mode is employed to detect a predetermined first liquid level h1 and a second liquid level h2 higher than the first liquid level h1.

The halt sensor 16 is, like the liquid-level sensor 15, for detecting the liquid level of the liquid formulation stored in the atomization tank 11 interior, but as later-described, is for detecting a liquid level for determining to forcibly halt the operation of the spraying apparatus 1.

As described above, the atomization tank 11 is arranged inside the region defined by the six columnar members 62 of the mounting unit 60, and also in the same manner, each instrument constituting the atomizing unit 10 is arranged inside the region defined by the six columnar members 62. In other words, when viewed in plan, the plurality of columnar members 62 is positioned outermost, and in the inner side of the region surrounded by the plurality of columnar members 62, each instrument is arranged to be positioned.

Configuration of Tank Unit 20

The tank unit 20 is for temporarily storing the liquid formulation to be supplied to the atomization tank 11 and is disposed above the atomizing unit 10. The tank unit 20 has a substantially rectangular parallelepiped shape, and has open on its upper surface an inflow port communicating with a liquid-formulation replenishing port 63*e* of a later-described top member 63. In addition, open on its bottom surface is a connection port connected to a liquid-formulation supply tube 42 of the supply unit 40. The tank unit 20 is fixed to the columnar members 62 by known means such as screw-fastening so as to be arranged inside the region defined by six columnar members 62 of the later-described mounting unit 60. In this situation, a flange part may be provided on the outer face of the tank unit 20, so that the flange part establishes connection to the columnar members 62. Substantially at the center of the tank unit 20, vertically formed is a recess 20*a*, which is configured such that a supply pipe 43 that supplies the fine particles and the conveyance air from the atomization tank 11 to the spouting unit 30 can pass through this recess 20*a*. The capacity of the tank unit 20 is larger than the capacity of the atomization tank 11, which enables a single replenishment of the liquid formulation to the tank unit 20 to supply the liquid formulation to the atomization tank 11 multiple times, thereby making it possible to continue operation over a long time.

The tank unit 20 is formed of polyethylene terephthalate (PET), like the atomization tank 11.

Configuration of Spouting Unit 30

Figure 3A:
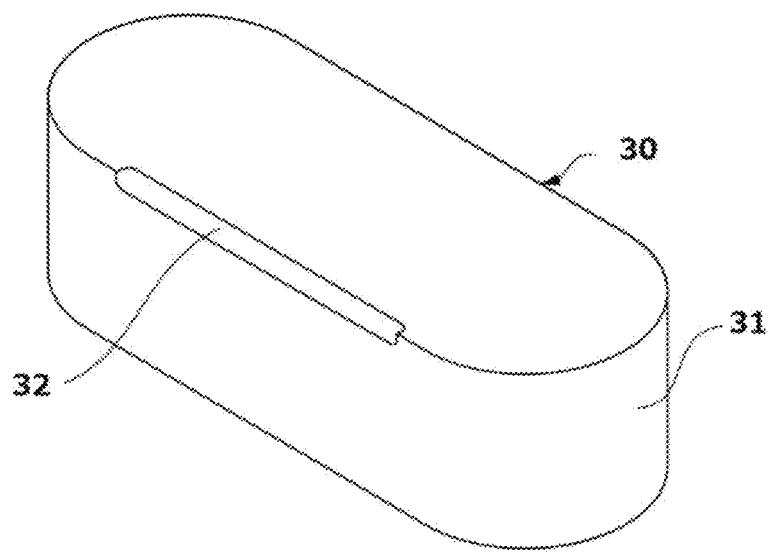
FIG. 3A is a perspective view of a spouting unit 30 for the spraying apparatus 1 involving the core embodying mode.
Figure 3B:
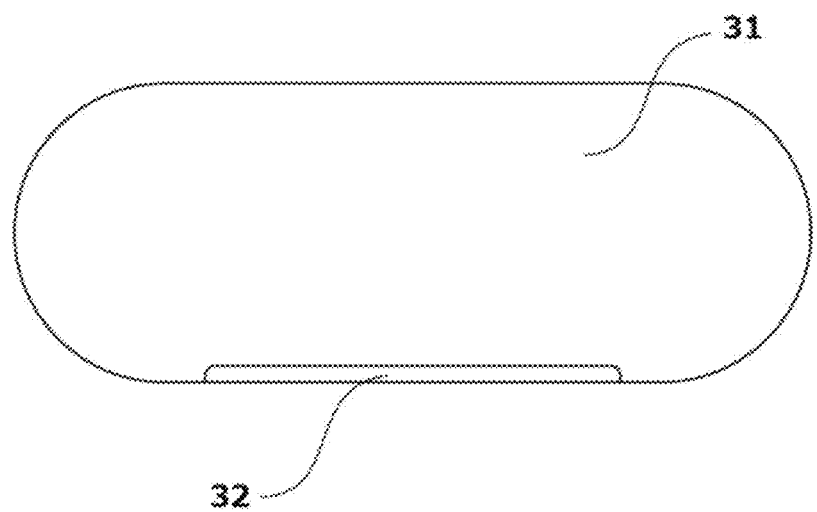
FIG. 3B is a plan view of the spouting unit 30 for the spraying apparatus 1 involving the core embodying mode.
Figure 3C:
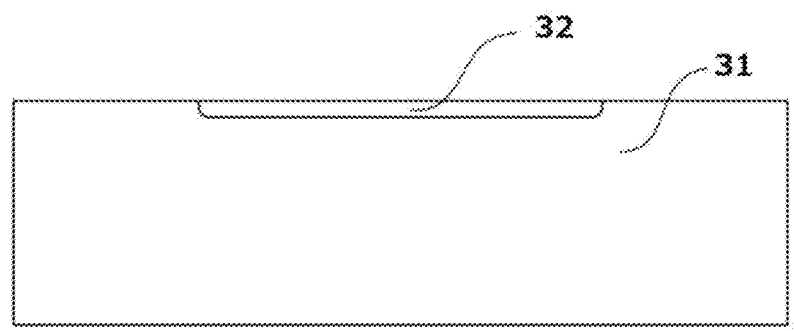
FIG. 3C is an elevational view of the spouting unit 30 for the spraying apparatus 1 involving the core embodying mode.
Figure 3D:
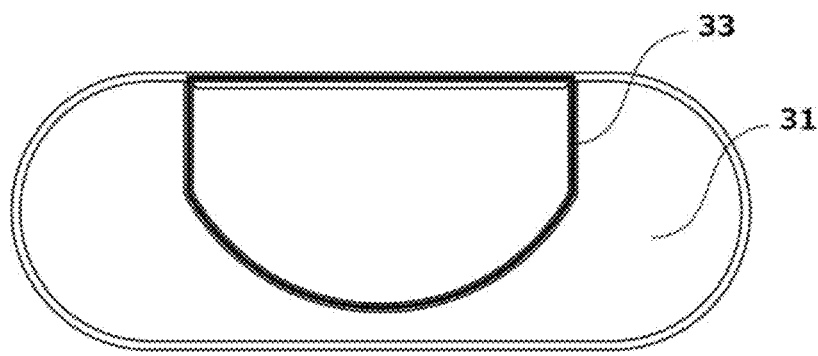
FIG. 3D is a bottom-face view of the spouting unit 30 for the spraying apparatus 1 involving the core embodying mode.

With reference to FIG. 3A-3D, the spouting unit 30 will be described. FIG. 3A shows a perspective view of the spouting unit 30, FIG. 3B a plan view of the spouting unit 30, FIG. 3C a front view of the spouting unit 30, and FIG. 3D a bottom view of the spouting unit 30.

The spouting unit 30 is for spouting the fine particles generated in the atomizing unit 10 together with the conveyance air, and is installed so as to protrude upward from the top member 63 arranged at the top of the mounting unit 60. The spouting unit 30, being formed of a bottomless, substantially cylindrical spouting element 31 having a predetermined width, depth, and height, has on its upper end a spray port 32 that inclines diagonally upward and is formed in the form of a slit widthwise. On the lower end of the spouting element 31, a plurality of lock hooks, not illustrated, that can be inserted into a locking recess 63*b* of the later-described top member 63, are formed.

Figure 5A:
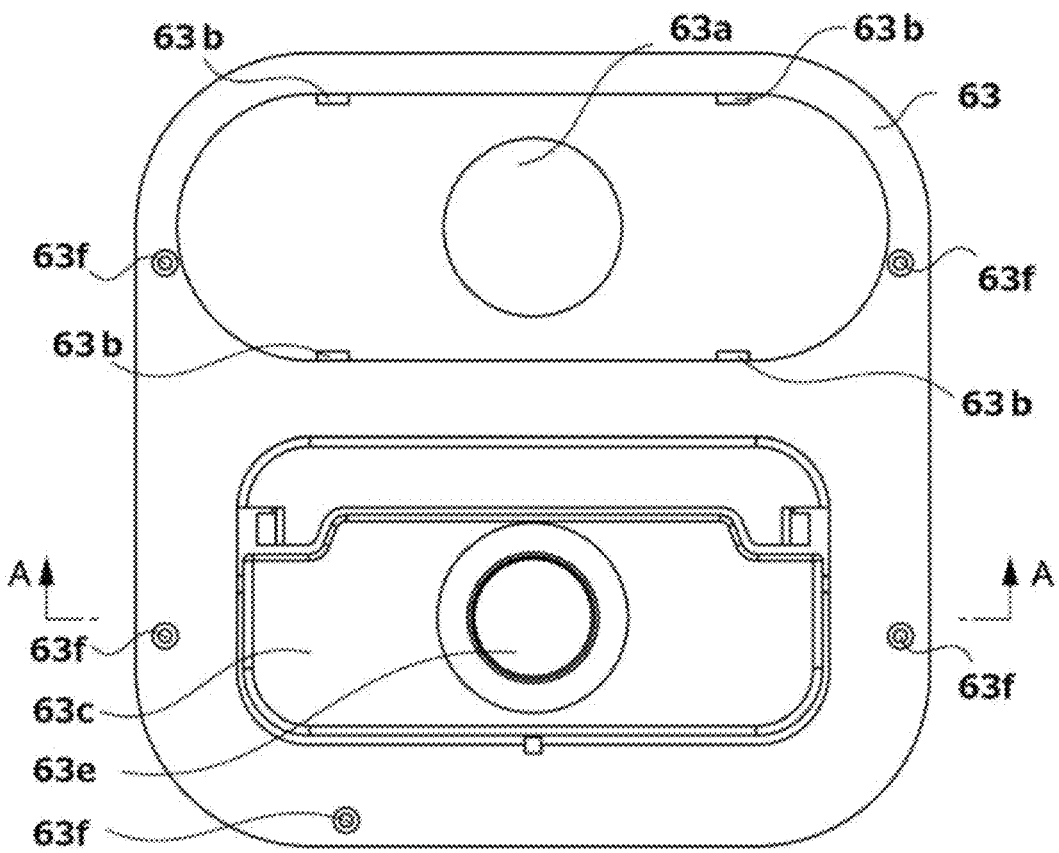
FIG. 5A is a plan view of a top component 63 involving the core embodying mode, in a state in which a top-component cover 63g has been removed.

Inside the spouting element 31, a partition wall 33 is provided protruding from the inner side of the top panel, and by connecting of the supply pipe 43 of the supply unit 40 to the region surrounded by the partition wall 33, fine particles and conveyance air from the atomizing unit 10 flow into the spouting unit 30 interior. In this regard, description is made with reference to a plan view illustrating a state in which a top member cover 63*g* of the top member 63 illustrated in FIG. 5A is removed. In the top panel of the top member 63, a connection port 63*a* connected to the supply pipe 43 of the supply unit 40 opens. At the same time, in the top panel of the top member 63, the locking recess 63*b* to be locked to the locking hook, not illustrated, formed on the lower end part of the spouting unit 30, is formed. Then, when the locking hook of the spouting unit 30 is locked to the locking recess 63*b* of the top member 63, the lower end of the partition wall 33 seals and adheres to the periphery of the connection port 63*a* in the top member 63, and the interior region of the partition wall 33 and the supply pipe 43 of the supply unit 40 are connected via the connection port 63*a*.

On the upper end of the interior region of the partition wall 33, the spray port 32 in the form of a slit inclined diagonally upward is formed, and the fine particles and the conveyance air that has flowed into the interior region of the partition wall 33 through the connection port 63*a* are sprayed through the spray port 32.

Configuration of Supply Unit 40

With reference to FIG. 1A-1D again, the configuration of the supply unit 40 will be described.

As illustrated in FIGS. 1B to 1D, the supply unit 40 is constituted by the liquid-formulation supply pump 41 for supplying the liquid formulation stored in the tank unit 20 to the atomizing unit 10; the liquid-formulation supply tube 42 that is connected to the liquid-formulation supply pump 41 and circulates the liquid formulation between the tank unit 20 and the atomizing unit 10; and the supply pipe 43 supplies the fine particles generated in the atomizing unit 10 and the conveyance air to a spraying unit.

The liquid-formulation supply tube 42 connects a connection port, not illustrated, and the inlet of the liquid-formulation supply pump 41 formed in the bottom surface of the tank unit 20, and also connects the outlet of the liquid-formulation supply pump 41 and the supply port 11*a* formed in the top panel of the atomization tank 11.

In other words, by utilizing the liquid-formulation supply pump 41 and the liquid-formulation supply tube 42, the liquid formulation stored in the tank unit 20 can be supplied into the atomization tank 11 interior through the supply port 11*a* as needed.

In the present embodying mode, a tube pump is employed as the liquid-formulation supply pump 41, but the present invention is not limited to this.

The supply pipe 43 connects the send-out port 11*c* formed in the top panel of the atomization tank 11 and the connection port 63*a* of the top member 63.

In other words, the fine particles generated in the atomization tank 11 are send out through the send-out port 11*c* together with the conveyance air, circulate in the supply pipe 43 and through the connection port 63*a* of the top member 63, flow into the interior region of the partition wall 33 formed in the spouting unit 30, and sprayed through the spray port 32.

In the present embodying mode, the supply pipe 43 is constituted by an accordion-fold flexible tube, but is not limited to this. In addition, the supply pipe 43 passes through a vertical recess formed substantially at the center of the tank unit 20, and connects the send-out port 11*c* and the connection port 63*a*.

Configuration of Control Unit 50

The control unit 50 is for controlling driving of the blower 13 and the driving of the liquid-formulation supply pump 41, and is constituted by known circuits, switches, or the like.

Configuration of Mounting Unit 60

Figure 4A:
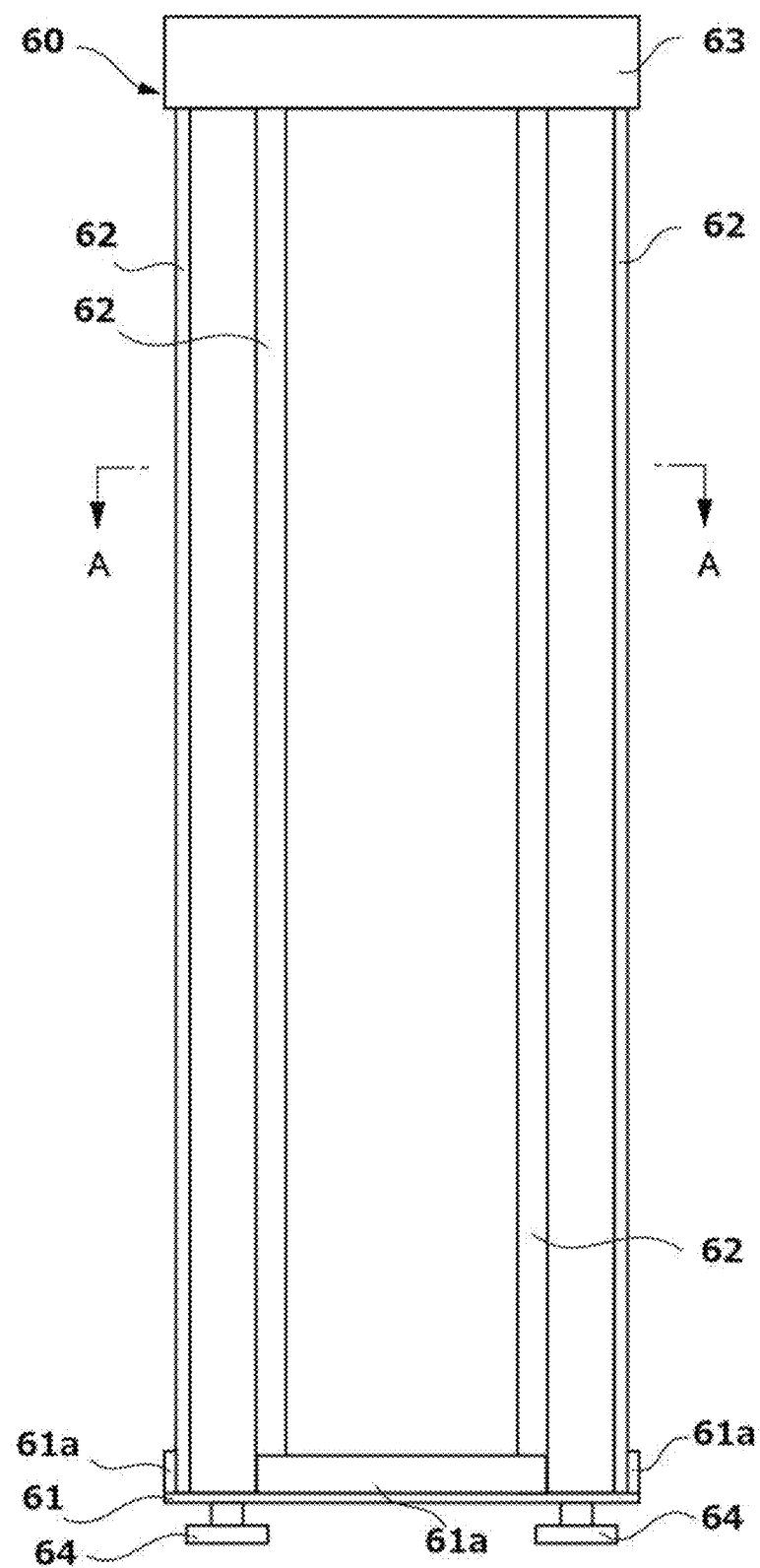
FIG. 4A is an elevational view of a mounting unit 60 involving the core embodying mode.
Figure 4B:
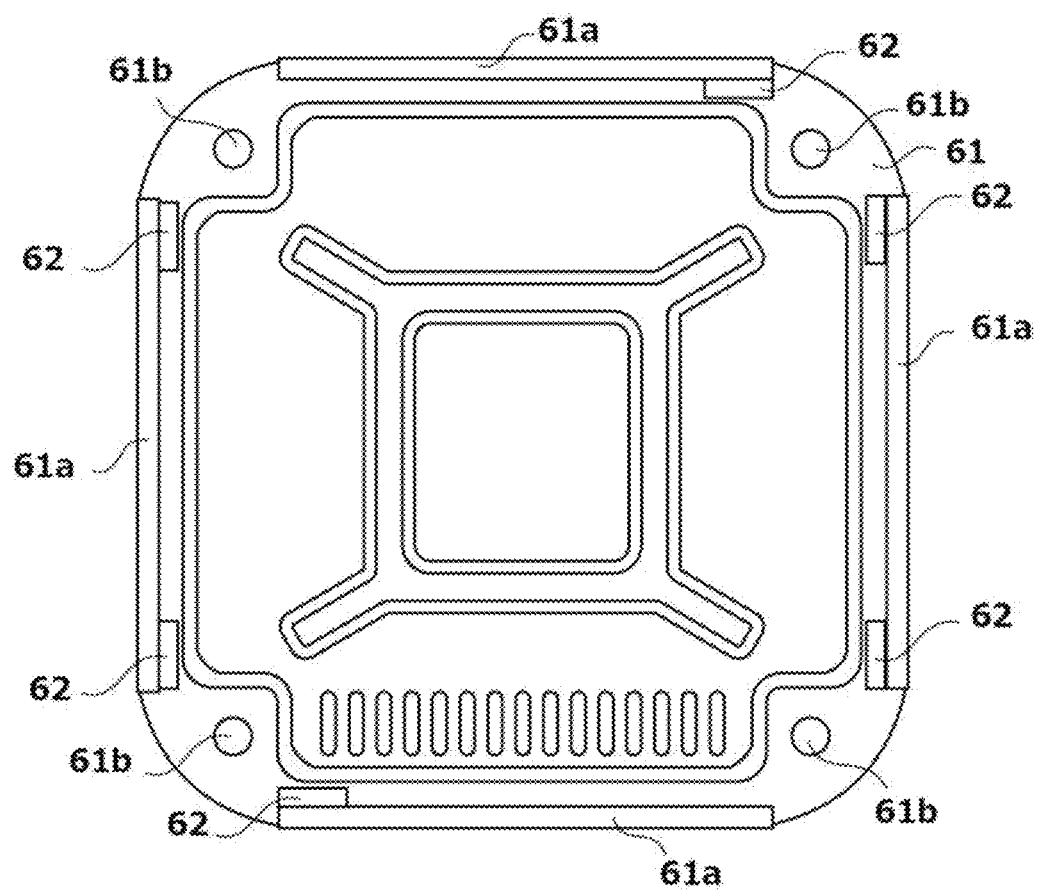
FIG. 4B is a cross-sectional view along A-A in FIG. 4A.
Figure 4C:
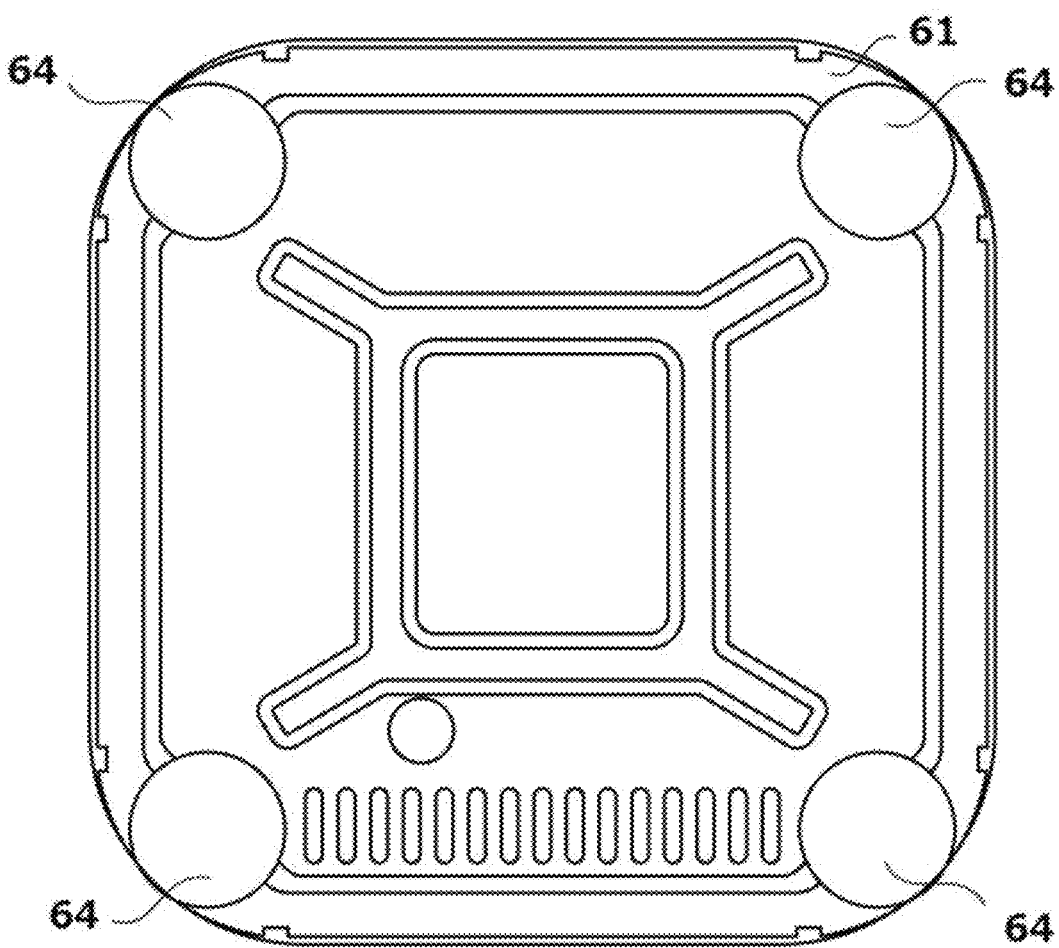
FIG. 4C is a bottom-face view of a base component 61 involving the core embodying mode.

With reference to FIG. 4A-4C, the mounting unit 60 will be described. FIG. 4A shows a front view of the mounting unit 60, FIG. 4B shows a sectional view along A-A in FIG. 4A, and FIG. 4C shows a bottom view of a base member 61.

The mounting unit 60 is for fixing the above units and members, and is constituted by a lower-part base 61, a plurality of columnar members 62, a top member 63, and a plurality of leg parts 64.

The lower-part base 61, being a planar rectangular tabular member located at the lower end part of the mounting unit 60, fixes the atomization tank 11, and also fixes the lower end parts of the plurality of columnar members 62. In the present embodying mode, on four sides of the lower-part base 61, raised parts 61*a* projecting upward are provided, and to each raised part 61*a*, the lower end parts of a plurality of columnar members 62 are fixed by screw-fastening, not illustrated. In addition, at four corners of the lower-part base 61, connection ports 61*b* to connect the leg parts 64 for installing the spraying apparatus 1 on a floor is provided. An internal thread is formed in the connection ports 61*b*, and an external thread part formed in the leg portion 64 is rotatably connected thereto.

The columnar members 62 being a plurality of columnar members arranged substantially perpendicularly, are members for defining the region on the inner side of the region defined by plurality of columnar members as a region where each unit is arranged, and also for fixing each unit. As illustrated in FIG. 4B, in the present embodying mode, six columnar members 62 are utilized to define the interior region where each unit is arranged. Each columnar member 62 has the lower end part fixed to the raised part 61*a* of the lower-part base 61, and the upper end part is fixed to the top member 63 by screw-fastening, not illustrated. In other words, the six columnar members 62 connect the lower-part base 61 and the top member 63. In FIGS. 4A and 4B, for better understanding, the thicknesses of the raised part 61*a* and the columnar member 62 are enlarged.

In the middle part of the columnar members 62, a fixing part, not illustrated, for fixing the tank unit 20, the control unit 50, and the like is disposed.

In particular, above the columnar member 62, a plurality of insertion holes, not illustrated, through which bolts serving as one of functions of the fixing parts for fixing the tank unit 20 can be inserted are disposed at the same height, and by screwing the bolts into internal threads provided at a predetermined height of the unit 20, the tank unit 20 can be fixed to the columnar member 62.

In this way, by arranging each instrument in the region surrounded by the plurality of perpendicularly arranged columnar members 62, each instrument is arranged so as to be vertically stacked. Since the columnar member 62 is a member disposed outmost when viewed in plan, it is possible to dispose the later-described cover member 80 to wrap around the columnar member 62. In this situation, since the cover member 80 has a form without unevenness, the spraying apparatus 1 attached to the cover member 80 can obtain a neat appearance suitable for various environments.

Next, the top member 63 will be described with reference to FIG. 5A-5E. FIG. 5A shows a plan view of the top member 63 in a state with the top member cover 63g removed, FIG. 5B a sectional view along the A-A in FIG. 5A, FIG. 5C a bottom view of the top member 63, FIG. 5D a plan view of the top member cover 63g, and FIG. 5E a perspective view of the top member 63 and the spouting unit 30 in replenishing of the liquid formulation.

Figure 5B:
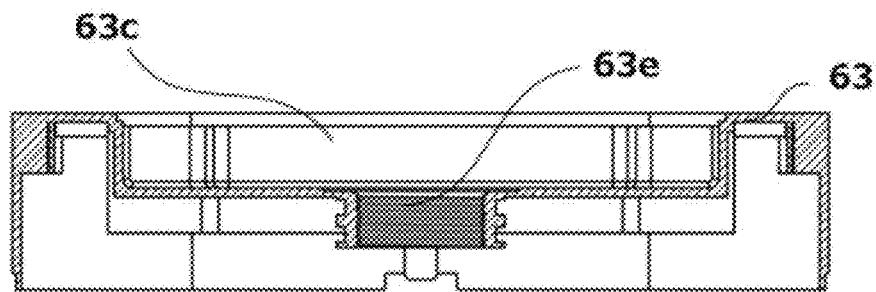
FIG. 5B is a cross-sectional view along A-A in FIG. 5A.

The top member 63, being a member positioned at the top of the mounting unit 60, is a member that is fixed to the upper end part of each columnar member 62, and also fixes the spouting unit 30 at the top of the entire spraying apparatus 1. As illustrated in FIGS. 5B and 5E, the top member 63 is composed of a tubular member having side walls, and having a bottomless, substantially rectangular planar shape with rounded corners.

Figure 5C:
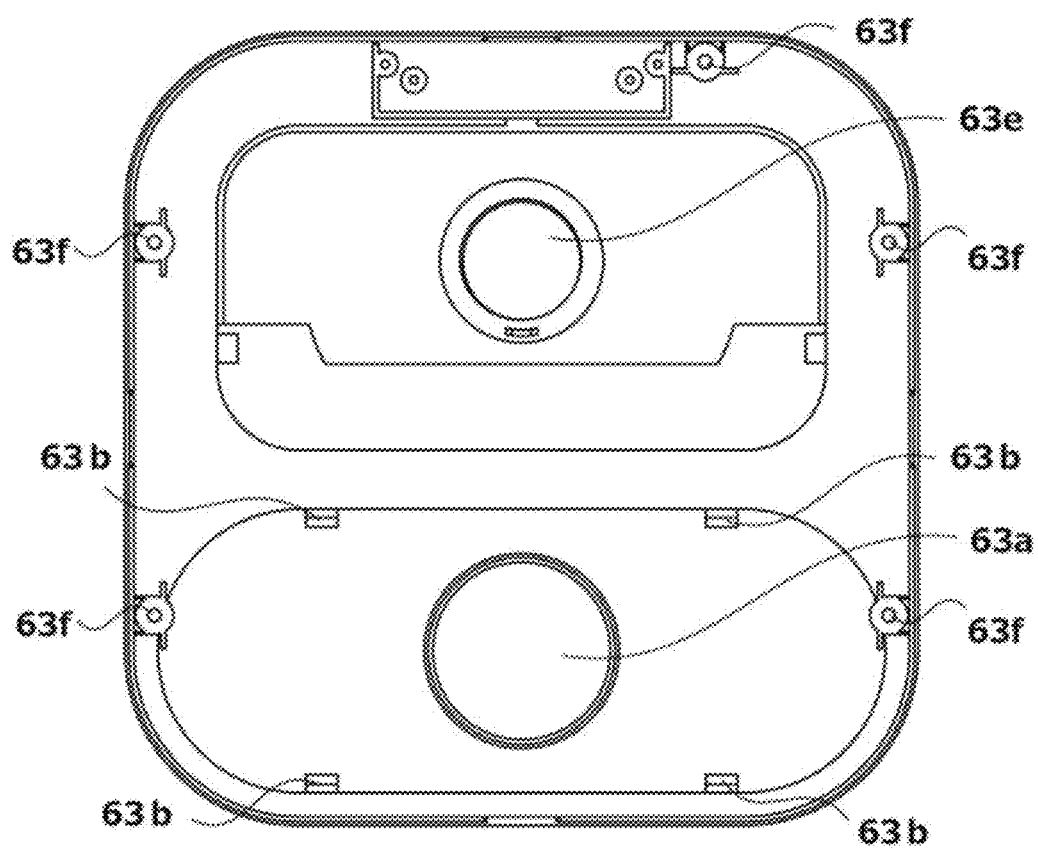
FIG. 5C is a bottom-face view of the top component 63 involving the core embodying mode.
Figure 5D:
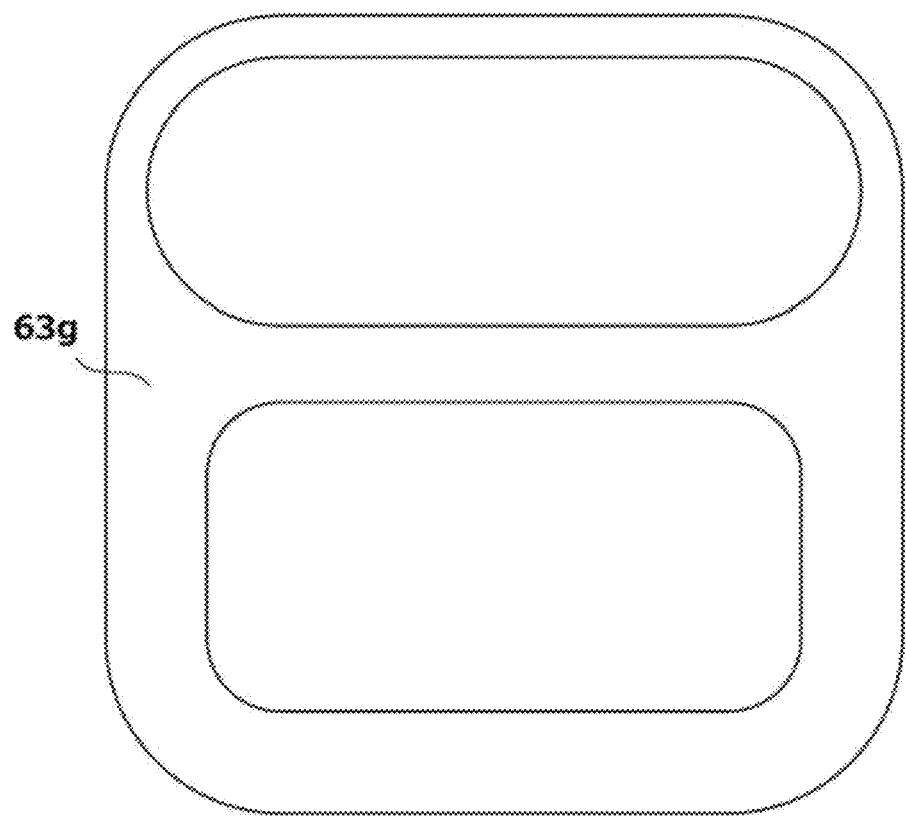
FIG. 5D is a plan view of the top-component cover 63g involving the core embodying mode.
Figure 5E:
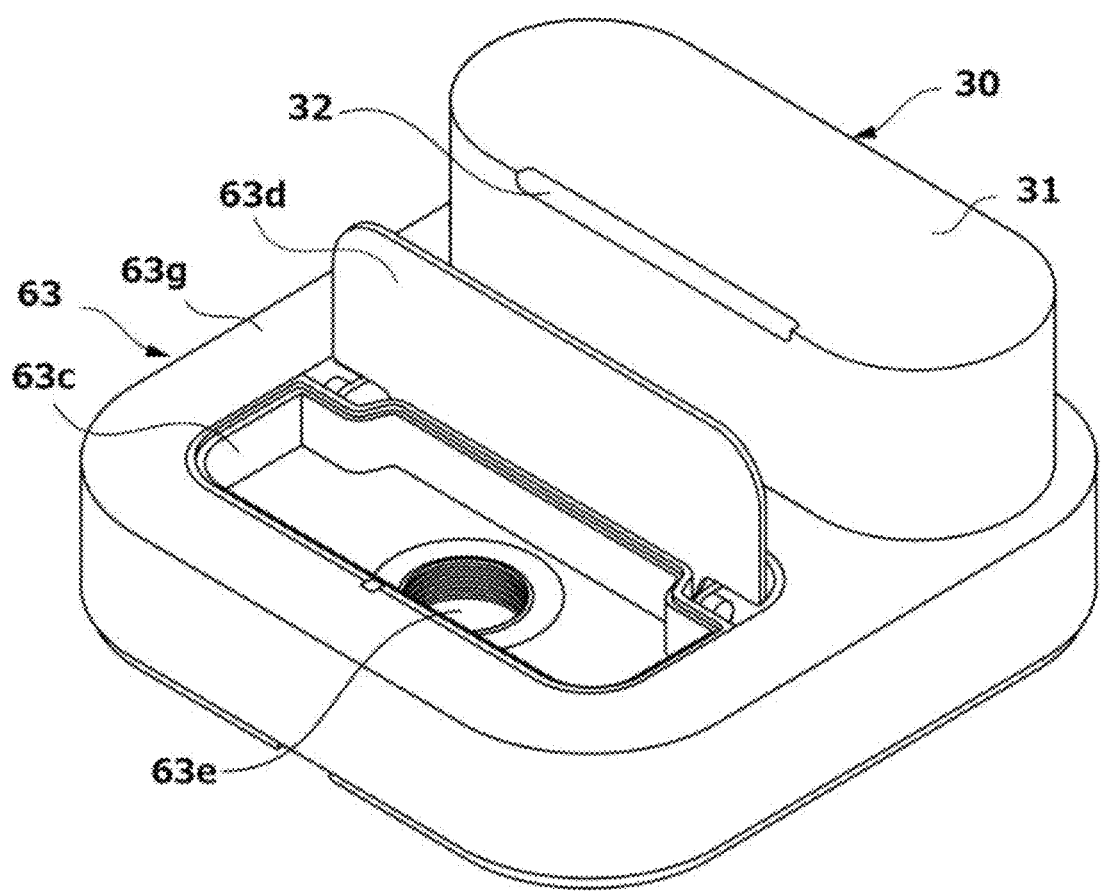
FIG. 5E is a perspective view of the top component 63 and the spouting unit 30 during liquid-formulation replenishment.

As illustrated in FIGS. 5A and 5C, open in the top panel of the top member 63 is a connection port 63a that is connected to the supply pipe 43 of the supply unit 40. At the same time, in the top panel of the top member 63, formed is a locking recess 63b to which the locking hook, not illustrated, form on the lower end part of the spouting element 31 is locked.

Furthermore, in the top panel of the top member 63, the top panel recess 63c the height of which is locally lowered downward, and the door-lid 63d that can be opened and closed that covers the top panel recess 63c are provided, and in the top panel recess 63c, the liquid-formulation replenishing port 63e connected to the inflow port, not illustrated, form in the upper surface of the tank unit 20 is provided. Formed in the inner face of the liquid-formulation replenishing port 63e is an internal thread, with which a cap member, not illustrated, having an external thread part is configured to screw and engage.

Connection between the top member 63 and the plurality of columnar members 62 is carried out by inserting bolts, not illustrated, through a plurality of screw holes 63f provided in the top panel, and screwing this bolt to internal threads, not illustrated, provided on the upper end of each columnar member 62. Alternatively, instead of providing the columnar member 62 with an internal thread, a bolt and nut may be used for connection. After connecting the top member 63 and the columnar member 62, as illustrated in FIG. 5E, the top panel of the top member 63 is covered with the top member cover 63g illustrated in FIG. 5D.

Configuration of Power Supply Unit 70

The power supply unit 70 is a unit that is connected to a household or commercial power supply to supply power to each instrument. Specifically, the power supply unit 70 includes a cable connected to a power tap, a power switch 71 of the spraying apparatus 1 itself, and the like.

Configuration of Cover Member 80

The cover member 80 is a member that is arranged on the periphery of the plurality of columnar members 62 and covers each instrument.

Specifically, as illustrated in FIG. 1A, it is arranged wound on the periphery of the plurality of columnar members 62 so as to cover the height from below the top member 63 to the lower-part base 61. The cover member 80 is formed by inflecting an elastic stainless steel tabular member by bending.

Here, in configuring the spraying apparatus 1, since each instrument such as the atomizing unit 10 and the tank unit 20 is arranged in the region surrounded by the plurality of perpendicularly arranged columnar members 62, the columnar member 62 is disposed outermost when viewed in plan. Therefore, the cover member 80 can be arranged so as to be wound around the columnar members 62. In this situation, since the cover member 80 has a form without unevenness, the spraying apparatus 1 attached to the cover member 80 can obtain a neat appearance suitable for various environments.

Spraying Method Employing Spraying Apparatus 1

Next, with reference to a flowchart shown in FIG. 6, a method of atomizing liquid formulation employing a spraying apparatus 1 according to the present embodying mode will be described.

Step S100: Replenish Liquid Formulation

First, prior to starting of the spraying apparatus 1, a liquid formulation is replenished to the tank unit 20 (Step S100).

When replenishing the tank unit 20 with the liquid formulation, a user opens a door-lid 63d that can be opened and closed provided in the top panel of the top member 63, removes a cap, not illustrated, attached to the liquid-formulation replenishing port 63e, and pours the liquid formulation into the liquid-formulation replenishing port 63e formed in the top panel recess 63c. After replenishing with the liquid formulation, the cap is tightened and the door-lid 63d is closed.

In this way, since the liquid-formulation replenishing port 63e is covered with the door-lid 63d that can be opened and closed, the liquid-formulation replenishing port 63e can be covered with the door-lid 63d when not in use, so that appearance can be maintained. In particular, since the liquid-formulation replenishing port 63e is formed in the top panel recess 63c, when the door-lid 63d is closed, the top panel of the top member 63 has the same plane except for the spouting unit 30, thereby exhibiting a particularly excellent appearance.

Step S110: Start Suppling Liquid Formulation

In Step S100, when the tank unit 20 is replenished with the liquid formulation, the user connects a power cord, not illustrated, that constitutes the power supply unit 70 to a general household or commercial power supply, and then turns on a power supply switch 71 that likewise that constitutes the power supply unit 70. When the power switch 71 is turned on, the control unit 50 operates the liquid supply pump 41 to start supplying the liquid formulation supplied to the tank unit 20 to the atomization tank 11 (Step S110).

The liquid formulation stored in the tank unit 20 is supplied to the atomization tank 11 as follows. That is, the liquid formulation supply pump 41 is driven by a signal from the control unit 50, and accordingly the liquid formulation flows out through a connection port, not illustrated, formed in the bottom surface of the tank unit 20, passes through the liquid formulation supply tube 42 and the liquid formulation supply pump 41, and flows into the atomization tank 11 interior through the supply port 11a formed in the upper surface of the atomization tank 11.

Steps S120-S130: Determine Second Liquid Level—Halt Liquid Formulation Supply

At the same time as the supply of the liquid formulation begins in Step S110, the control unit 50 begins determination of the liquid level by the liquid-level sensor 15, determining whether the liquid level in the atomization tank 11 has reached a predetermined second liquid level h2 (Step S120).

If the liquid level detected by the liquid-level sensor 15 does not reach the second liquid level h2, that is, "N" in Step S120, the control unit 50 continues the supply by the liquid-formulation supply pump 41, whereas if the second liquid level h2 is reached, that is "Y" in Step S120, the control unit 50 halts the supply by the liquid-formulation supply pump 41 (Step S130).

Step S140: Atomization of Liquid Formulation

In Step S130, if the supply of the liquid formulation is halted, the control unit 50 begins the atomization of the liquid formulation in the atomizing unit 10 (Step S140). Beginning the atomization un in Step S140 may be controlled to be triggered by the liquid level detected by the liquid-level sensor 15 reaching the first liquid level h1. In that case, the atomization operation and the supply of the liquid formulation are performed at the same time, which is preferable because the atomization operation can be started early.

When atomization of the liquid formulation is carried out in the atomizing unit 10, the control unit 50 begins blowing of the conveyance air by the blower 13, and at the same time, begin the atomization of the liquid formulation by the atomizing device 12.

Figure 2B:
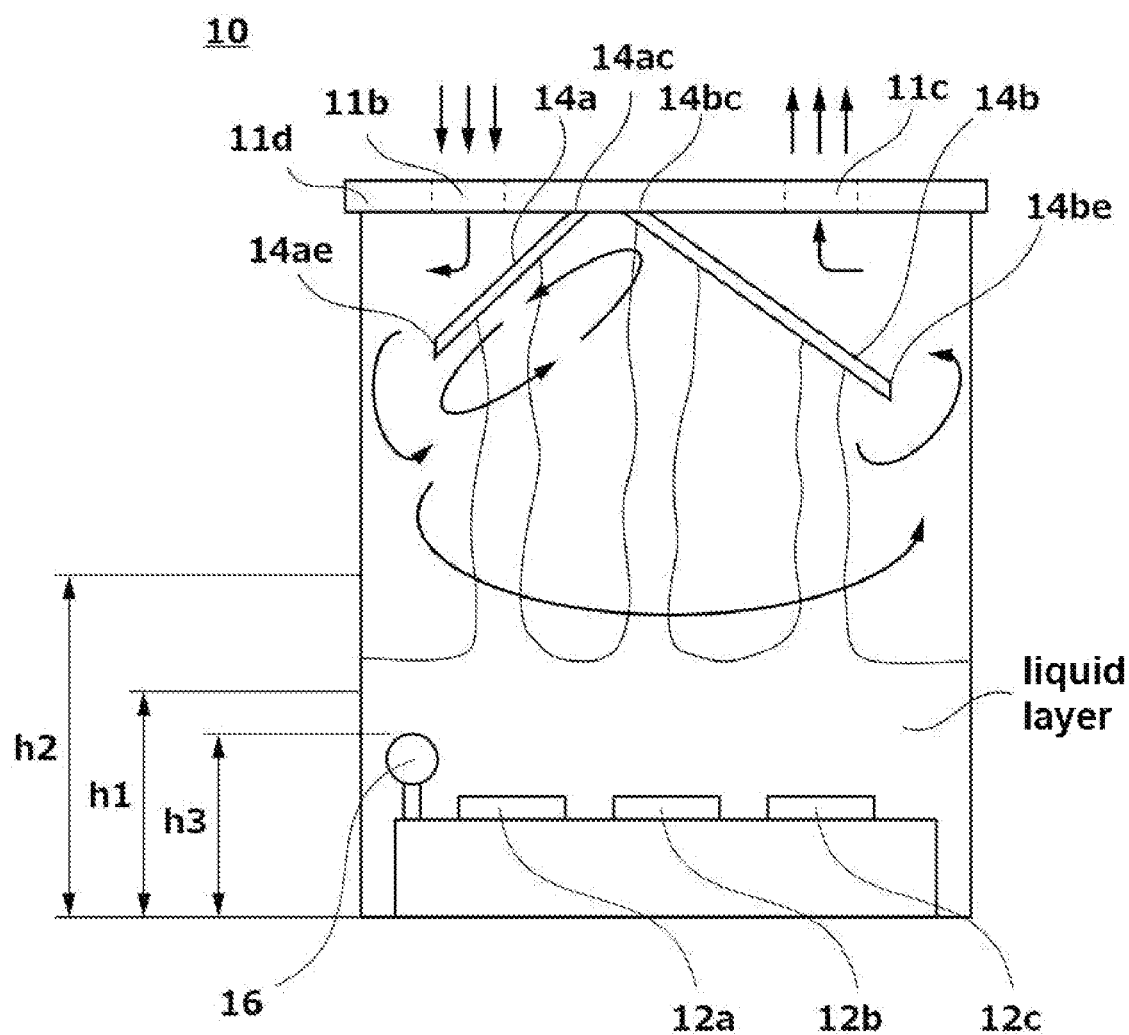
FIG. 2B is a schematic view of the atomization unit 10 involving the core embodying mode, in a state during use.

Along with the operation of the atomizing device 12, as illustrated in FIG. 2B, the liquid column rises above each of the ultrasonic vibrators 12a, 12b, 12c . . . . While the liquid column contains particles of various particle sizes, the liquid droplets of large particle diameter contained in the liquid column contact the baffle plates 14a and 14b arranged inclined diagonally downward above the ultrasonic vibrator for contact with the liquid column, flow downward, and flow back to the stored liquid layer, whereas only the mist droplets of small particle diameter float in the air.

In addition, along with the operation of the blower 13, the conveyance air is supplied downward from the blow port 11b, conveying and sending out the mist droplets of small particle diameter floating in the air from the send-out port 11c.

At this time, since the baffle plate 14a provided along one widthwise end of the atomization tank 11 is arranged underneath the blow port 11b and above the ultrasonic vibrators 12a and 12d along one widthwise end, the conveyance air supplied through the blower 13 is prevented from directly reaching the liquid surface and the liquid column, and also the liquid column and the liquid droplets rising from the liquid surface is prevented from flowing from the blow port 11b and directly reaching the blower 13. Therefore, atomization of the liquid formulation and supply of the conveyance air function without interfering with each other, thereby ensuring the performance of particle size sorting.

In addition, the conveyance air supplied through the blower 13 collides against one side of the surface of the baffle plate 14a, and flows along one side of the surface of the baffle plate 14a, and then pressure loss occurs, resulting in drop in pressure for conveying particles. Because the pressure of the conveyance air drops, from the liquid formulation that has been separated into liquid droplets and tiny particles by colliding against the baffle plates 14a and 14b, only fine particles still smaller than particles of size at the level allowing normal conveyance are conveyed by the conveyance air.

In addition, when the conveyance air that has flowed along one side of the surface of the baffle plate 14a flows out between the edge piece 14ae and the surface along one end of the atomization tank 11, a negative pressure region forms along the baffle plate 14a on the other side of the surface, that is, the region that the liquid column comes into contact with. In the negative pressure region, the pressure of the conveyance air drops still further, and therefore particles other than fine particles that are of extraordinarily tiny particle diameter cannot be conveyed, meaning they fall to the liquid surface below. Consequently, fine particles of particle diameter tiny to a level that can give rise to Brownian motion can alone be conveyed downstream by the conveyance air.

A mechanism like this affords a spraying apparatus that, more than simply receiving liquid columns at the baffle plate makes possible conveying minute particles by means of conveyance air, and enables the selective spraying of only fine particles that are tiny to a level that can give rise to Brownian motion.

In addition, the baffle plate 14a is arranged inclined diagonally downward, with one end having the connection piece 14ac (first connection piece) connected to the top panel 11d of the atomization tank 11, and the other end having the edge piece 14ae (first edge piece) spaced apart at a predetermined spacing from the lateral surface along one widthwise end of the atomization tank 11. In order to allow the conveyance air supplied through the blower 13 to pass through the outer peripheral side in the atomization tank 11, it is arranged protruding from the inside toward the outside.

Owing to this sort of structure of the baffle plate 14a, the conveyance air supplied downward through the blow port 11b changes its flow direction diagonally downward according to the orientation in which baffle plate 14a is arranged, and having passed through the gap formed between the lateral surface along one widthwise end of the atomization tank 11 and the edge piece 14ae of the baffle plate 14a, arrives at the bottom portion of the atomization tank 11 near the liquid layer. The conveyance air that has reached the bottom switches the direction toward the lateral surface along the other widthwise end, and circulates in the vicinity of the liquid surface toward the lateral surface along the other widthwise end of the atomization tank 11. Then, it switches the direction upward in the vicinity of the lateral surface along the other widthwise end of the atomization tank 11, and flows toward the send-out port 11c formed in the top panel 11d. In addition, having passed through the gap formed between the lateral surface along one widthwise end of the atomization tank 11 and the other end part of the baffle plate 14a, part of the conveyance air winds in on the surface along the liquid-column receiving side of the baffle plate 14a, and then forms a swirling flow in the atomization tank 11 and flows out through the send-out port 11c.

In this way, the conveyance air supplied downward through the blow port 11b forms a gently swirling flow in the interior part of the atomization tank 11 according to the orientation in which baffle plate 14a is arranged, part of it winds in on the surface along the liquid-column receiving side, and then part of it, having passed through the outer peripheral side in the atomization tank 11 is sent out through the send-out port 11c.

Since the conveyance air supplied through the blow port 11b passes through the outer peripheral side in the atomization tank 11 and forms a gently swirling flow, owing to the centrifugal-force effect that accompanies the production of the swirling flow, the minute particles are further separated from even more minute fine particles, and the fine particles alone are conveyed on the conveyance air.

Furthermore, in the present embodying mode, the blow port 11*b* and the send-out port 11*c* are provided on the top panel 11*d* of the atomization tank 11 and in locations on opposite sides from each other, with the baffle plate 14*a* being put in between.

Therefore, the swirling flow in which the baffle plate 14*a* is interposed can be formed, and thus the effect of centrifugal separation by the swirling flow can be heightened.

The atomizing unit 10 in the present embodying mode designed in this way enables, by collaboration between the blower 13 and the baffle plate 14*a*, selectively generating and sending out only fine particles that are tiny to a level that can give rise to Brownian motion.

In addition, in the present embodying mode, the baffle plate 14*b* is arranged inclined diagonally downward, toward the opposite side from the baffle plate 14*a*, in such a manner that one end has a connection piece 14*bc* (second connection piece) connected to the top panel of the atomization tank 11, and the other end has an edge piece 14*be* (second edge piece) arranged spaced apart at a predetermined spacing from the lateral surface along the other widthwise end of the atomization tank 11, that is, on the side opposite from the side where the baffle plate 14*a* is arranged.

The baffle plate 14*b* is arranged underneath the send-out port 11*c* and above the ultrasonic vibrators 12*c* and 12*f* along the other widthwise end. Therefore, the liquid droplets of large particle diameter contained in the liquid column produced by the ultrasonic vibrators 12*c* and 12*f* come into contact with the lower surface of the baffle plate 14*b*, flow downward, and flow back to the stored liquid layer, whereas only the mist droplets of small particle diameter float in the air.

At this time, because the pressure of the conveyance air has dropped due to contact with the baffle plate 14*a*, only fine particles still smaller than particles of size at the level allowing normal conveyance are conveyed by the conveyance air. In this way, also among particles produced in the vicinity of the baffle plate 14*b*, only fine particles of tiny diameter can be selectively conveyed.

In addition, the blow port 11*b* is provided to one widthwise end of the connection piece 14*ac* of the baffle plate 14*a* in the top panel 11*d* of the atomization tank 11, and meanwhile the send-out port 11*c* is provided to the other widthwise end of the connection piece 14*bc* of the baffle plate 14*b*, by which the swirling flow formed in the atomization tank 11 interior becomes so large that is formed throughout the entire atomization tank 11 with the baffle plate 14*a* and baffle plate 14*b* interposed. Therefore, the selection of fine particles by the centrifugal force of the conveyance air is further enhanced, fine particles that are minute to a level that can give rise to Brownian motion alone can be reliably selected and sprayed.

Steps S150-S160: Determine First Liquid Level—Begin Replenishment of Liquid Formulation Reference is made back to the flowchart in FIG. 6. In Step S140, when the atomization of the liquid formulation begins, the control unit 50 begins to determine the liquid level by the liquid-level sensor 15, determining whether the liquid level in the atomization tank 11 has fallen below the first liquid level h1 (Step S150).

If the liquid level detected by the liquid-level sensor 15 has secured the first liquid level h1, that is, "N" in Step S150, the control unit 50 continues the atomization intact, and if it falls below the first liquid level h1, that is "Y" in Step S150, the control unit 50 begins replenishment of the liquid formulation by the liquid-formulation supply pump 41 (Step S160).

The replenishment of the liquid formulation in Step S160 is carried out by operating of the liquid-formulation supply pump 41, as in Step S110. In this case, the atomization tank 11 can be replenished with the liquid formulation by the liquid-formulation supply pump 41 at the same time while the atomization operation is continued.

In particular, since the supply port 11*a* is formed above the baffle plate 14*b*, the liquid formulation supplied through the supply port 11*a* passes along the baffle plate 14*b*, and in a liquid state, fall to the liquid layer stored in the atomization tank 11 interior. That is, the liquid formulation supplied through the supply port 11*a* is replenished in the liquid layer without being affected by the ultrasonic vibration. Therefore, the liquid formulation can be replenished without affecting the fine-particle selection performance in the present embodying mode.

Steps S170-S180: Determine Second Liquid Level—Halt the Liquid Formulation Supply At the same time as the replenish of the liquid formulation begins in Step S160, the control unit 50 begins determination of the liquid level by the liquid-level sensor 15, determining whether the liquid level in the atomization tank 11 has reached a second liquid level h2 higher than the predetermined first liquid level h1 (Step S170).

If the liquid level detected by the liquid-level sensor 15 does not reach the second liquid level h2, that is, "N" in Step S170, the control unit 50 continues the supply by the liquid-formulation supply pump 41, whereas if the second liquid level h2 is reached, that is "Y" in Step S170, the control unit 50 halts the supply by the liquid-formulation supply pump 41 (Step S180).

Thereafter, until the user turns off the power switch 71, the processing may be controlled to return to Step S150 and repeat the processes from determination of the first liquid level to supply of the liquid formulation.

By doing so, the liquid level of the liquid formulation in the atomization tank 11 can be maintained between the first liquid level h1 and the second liquid level h2, allowing the user to automatically continue the operation over a long time without paying attention to the increase or decrease in the liquid level.

In addition, the control unit 50 may be configured so as to always determine, by utilizing the halt sensor 16, whether or not the liquid level has fallen below a third liquid level h3 lower than the first liquid level h1. If the halt sensor 16 detects that the liquid level has fallen below the third liquid level h3, the control unit 50 immediately halts the operation of the blower 13 and the atomizing device 12.

By doing so, it is possible to keep the atomizing device 12 from operating in situations where the liquid formulation is extremely scant, thereby preventing so-called empty-tank running.

In addition, at this time, the control unit 50 may be configured to notify, at the same time as halting the operation, the user of a state in which the apparatus is run on an empty tank by means of sounding an alarm sound or turning on a warning light. With this configuration, the user can realize an empty-tank running state.

Adjustment of Particle Diameter Employing Spraying Apparatus 1

Next, a method of adjusting the particle diameter of fine particles to be sprayed by employing the spraying apparatus 1 of the present embodying mode to a desired value will be described.

As described above, the control unit 50 can control the rpm of the blowing element of the blower 13 by controlling the voltage applied to the blower 13. Then, by raising the rpm of the blowing element, the particle diameter of the fine particles sprayed from the spray port 32 can be made smaller. Conversely, by lowering the rpm of the blowing element, the fine particles sprayed from the spray port can be made larger. The mechanism by which the particle diameter of the sprayed particles can be changed in accordance with the change in the rpm of the blowing element will be described below.

In general, when the rpm of the blowing element is controlled, the fanning volume changes as the rpm changes. For example, by raising the rpm of the blowing element, the fanning volume is increased, and by lowering the rpm, the fanning volume is decreased. However, since the air pressure itself does not change, the conveying capacity of the conveyance air does not change, and it is not possible to change the particle diameter of conveyable particles by changing the rpm.

On the other hand, in the present invention, since the blow port 11b for the conveyance air supplied from the blower 13 is arranged above the baffle plate 14a, the conveyance air supplied through the blow port 11b collides against the surface on one side of the baffle plate 14a, and pressure loss occurs.

By controlling the rpm of the blowing element in a state in which pressure loss in the conveyance air has been brought about, change in air pressure with respect to change in conveyance-air fanning volume can be made larger. For example, by raising the rpm of the blowing element, the fanning volume of the conveyance air is increased, thereby pressure loss produced by contact with the baffle plate 14a is increased, and therefore pressure of the conveyance air drops, and capacity for conveying particles is made smaller. Therefore, compared to before changing of the rpm, particles of tiny particle size are conveyed.

Conversely, by lowering the rpm of the blowing element, the fanning volume of the conveyance air is decreased, thereby pressure loss caused produced by contact with the baffle plate 14a is decreased, and therefore pressure of the conveyance air rises, and capacity for conveying particles is improved. Therefore, compared to before changing the rpm, particles whose diameter is large are conveyed In this way, by exploiting the increase or decrease in pressure loss, it is possible to change the particle diameter of the conveyable particles.

In addition, in the present embodying mode, the conveyance air, after having gone through the spacing formed between the edge piece 14ae of the baffle plate 14a and the atomization tank 11, winds in on the surface along the liquid-column receiving side in the baffle plate 14a and then arrives at the send-out port 11c, surrounding the baffle plate 14a gently swirling flow of the conveyance air directed to the send-out port.

By controlling the rpm of the blowing element, the fanning volume is changed, and therefore centrifugal force applied to the atomized particles is changed, that is, the particle diameter of conveyable particles can be changed. For example, by raising the rpm of the blowing element, the fanning volume of the conveyance air is increased, thereby the centrifugal force applied to the particles accompanying the swirling flow is increased, particles of relatively tiny particle diameter are separated, and therefore only particles of extraordinarily tiny particle diameter are conveyed.

Conversely, by lowering the rpm of the blowing element, the fanning volume of the conveyance air is reduced, thereby the centrifugal force applied to the particles accompanying the swirling flow is decreased, capacity for separating the particles is weakened, and particles whose diameter is large are made conveyable.

In this way, by controlling the rpm of the blowing element of the blower 13 by the control unit 50, it is made possible to spray fine particles of a desired particle size from the spray port 32.

Modification 1

Figure 6:
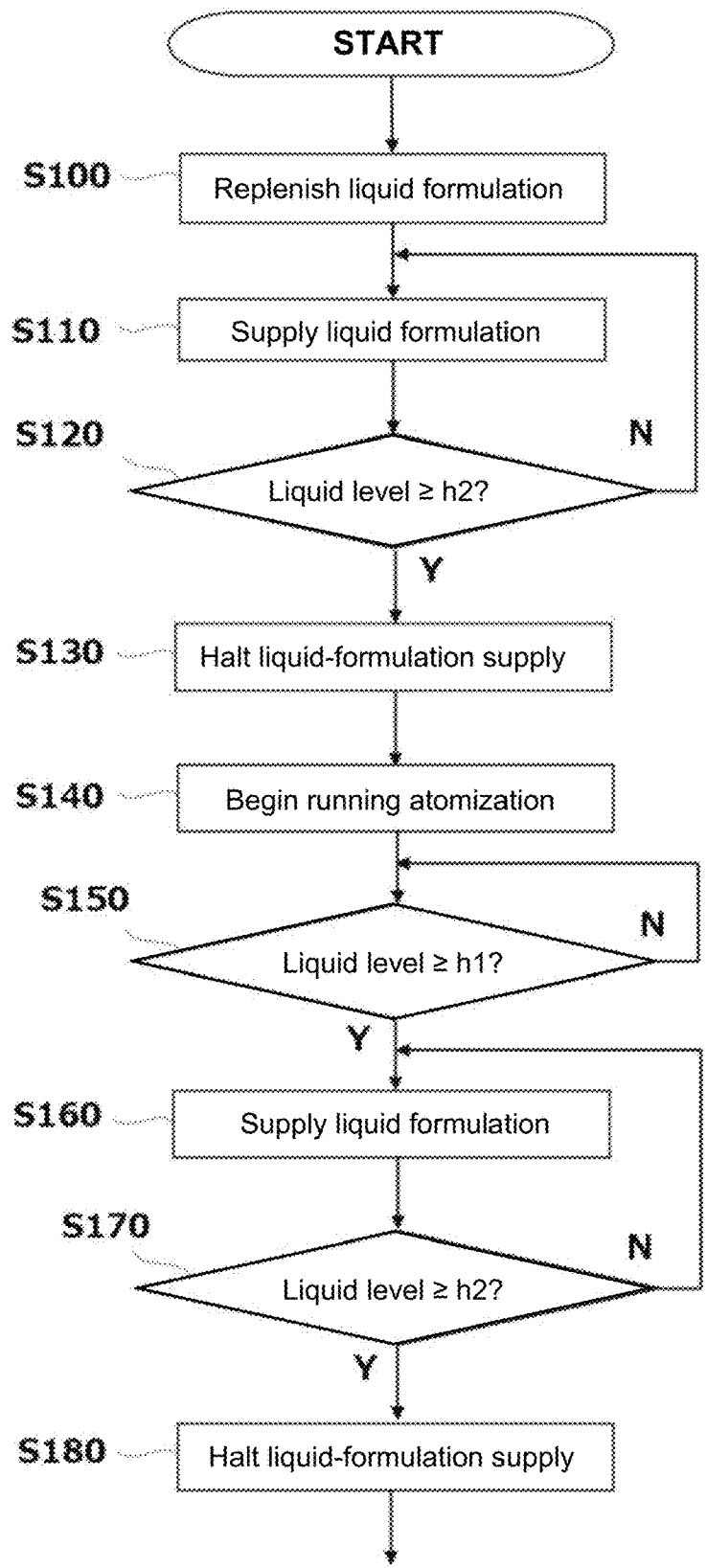
FIG. 6 is a flowchart of a liquid-formulation spraying method employing a spraying apparatus 1 involving the core embodying mode.

In Step S110 of the flowchart shown in FIG. 6, the liquid formulation is supplied to the atomization tank 11 from the tank unit 20 by utilizing the liquid-formulation supply pump 41, but a configuration in which in place of the liquid-formulation supply pump 41, a solenoid valve is employed to supply the liquid formulation.

In other words, in the midway through the liquid-formulation supply tube 42, a solenoid valve that can be opened and closed in response to a signal from the control unit 50 is arranged, such that when the control unit 50 issues an open signal, the solenoid valve is released to supply the liquid formulation. At this time, since the tank unit 20 is arranged beneath the atomization tank 11, the liquid formulation can be supplied exploiting gravity, and the liquid formulation can be supplied more rapidly and with less power consumption than by employing the liquid-formulation supply pump 41. In particular, when the liquid formulation is supplied to the atomization tank 11 at the time of start-up, by supply exploiting gravity, the time from turning on the power switch 71 until beginning atomization can be shortened, and an easy-to-use spraying apparatus 1 can be afforded.

Modification 2

With reference to FIG. 7A-7D, modification of the configuration of the atomizing unit 10 will be described. Instead of arranging inclined diagonally downward, the baffle plates 14a and 14b can be arranged perpendicularly downward from the top panel and then arranged inflecting horizontally toward the lateral surface of the atomization tank 11.

Figure 7A:
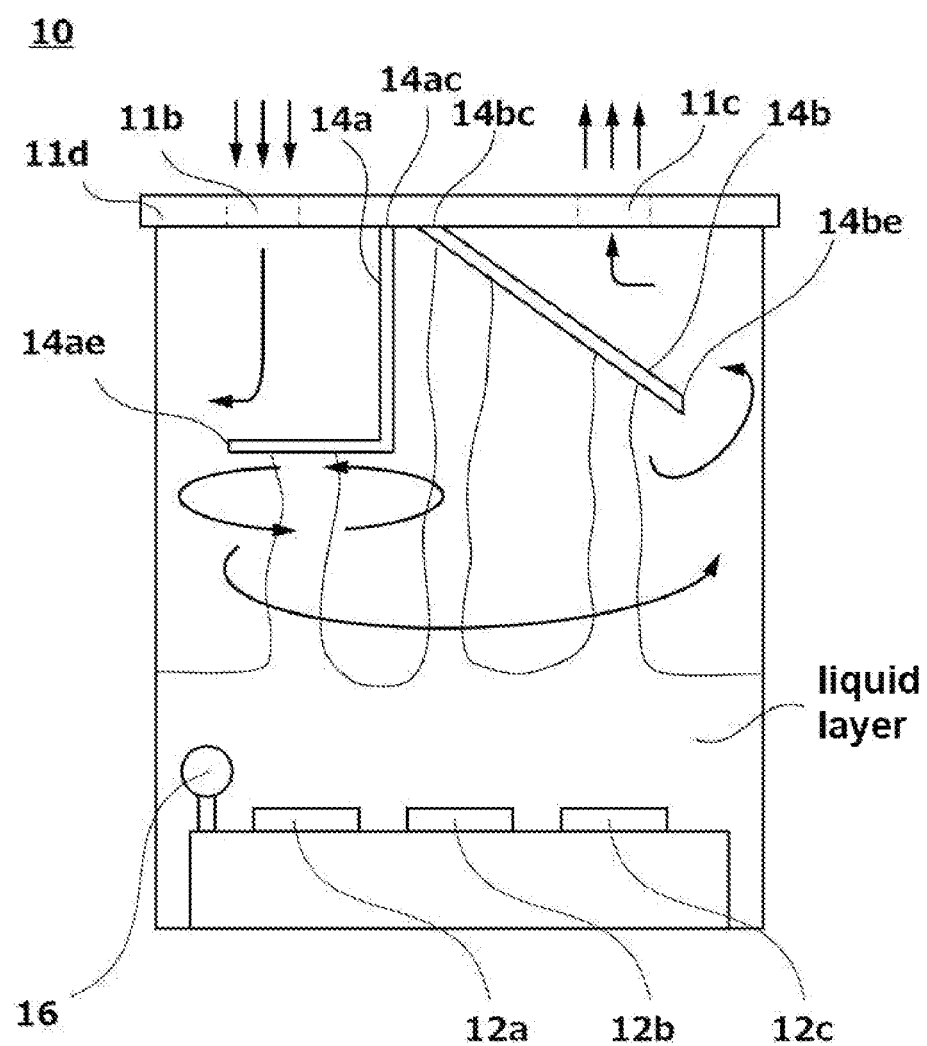
FIG. 7A is a schematic view of an atomization unit 10 involving Modification Example 2, in a state during use.
Figure 7B:
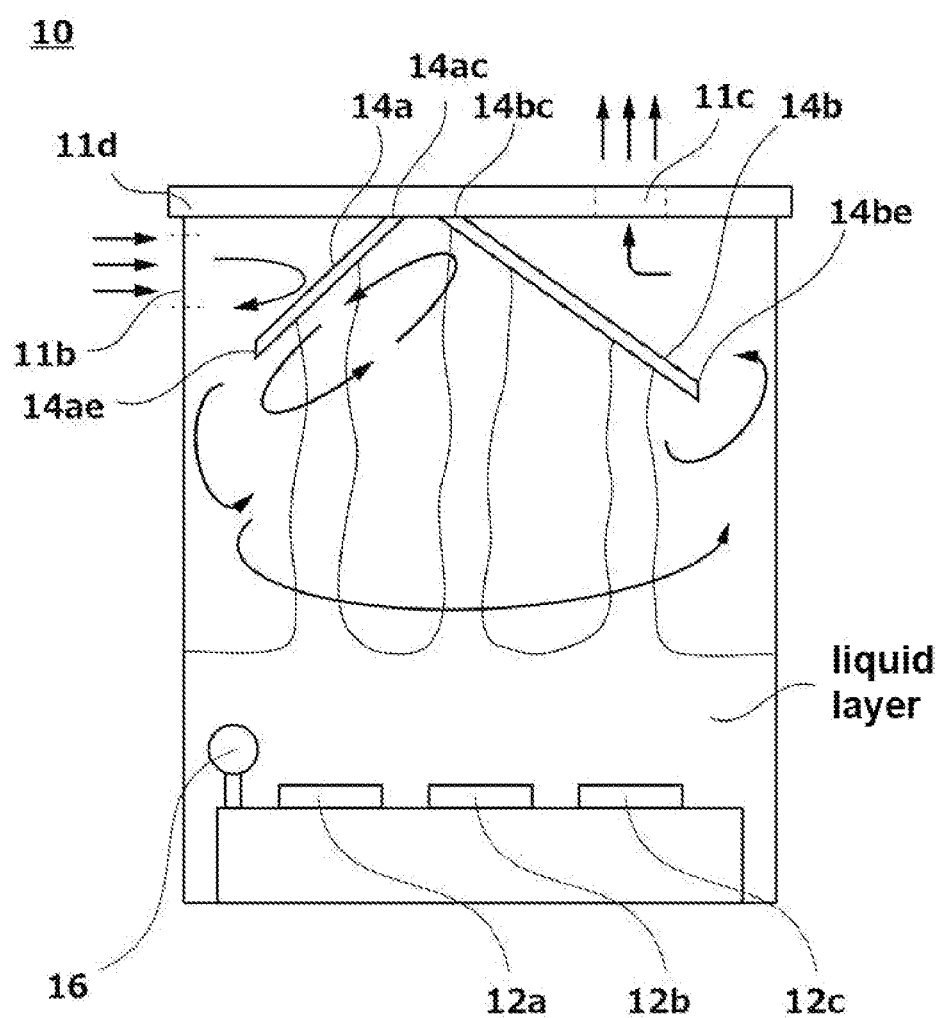
FIG. 7B is a schematic view of an atomization unit 10 involving Modification Example 3, in a state during use.
Figure 7C:
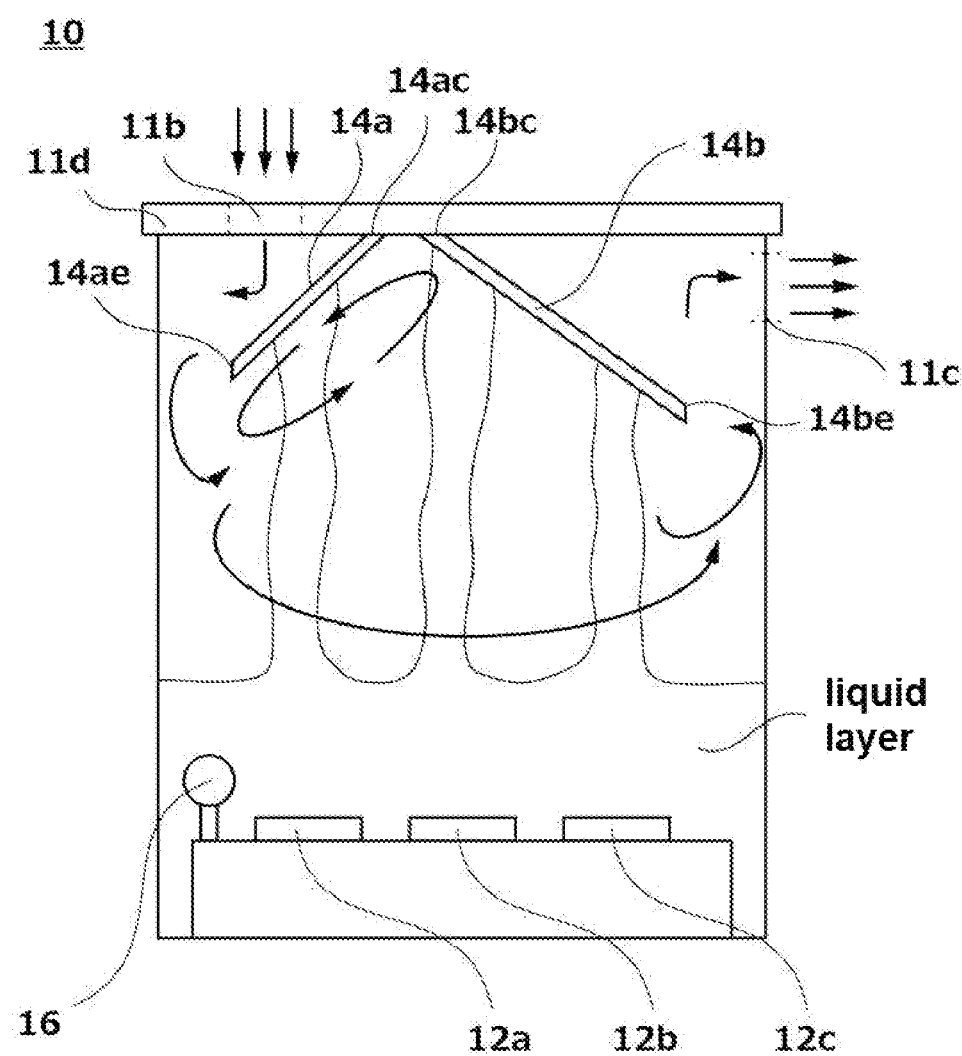
FIG. 7C is a schematic view of the atomization unit 10 involving Modification Example 3, in a state during use.
Figure 7D:
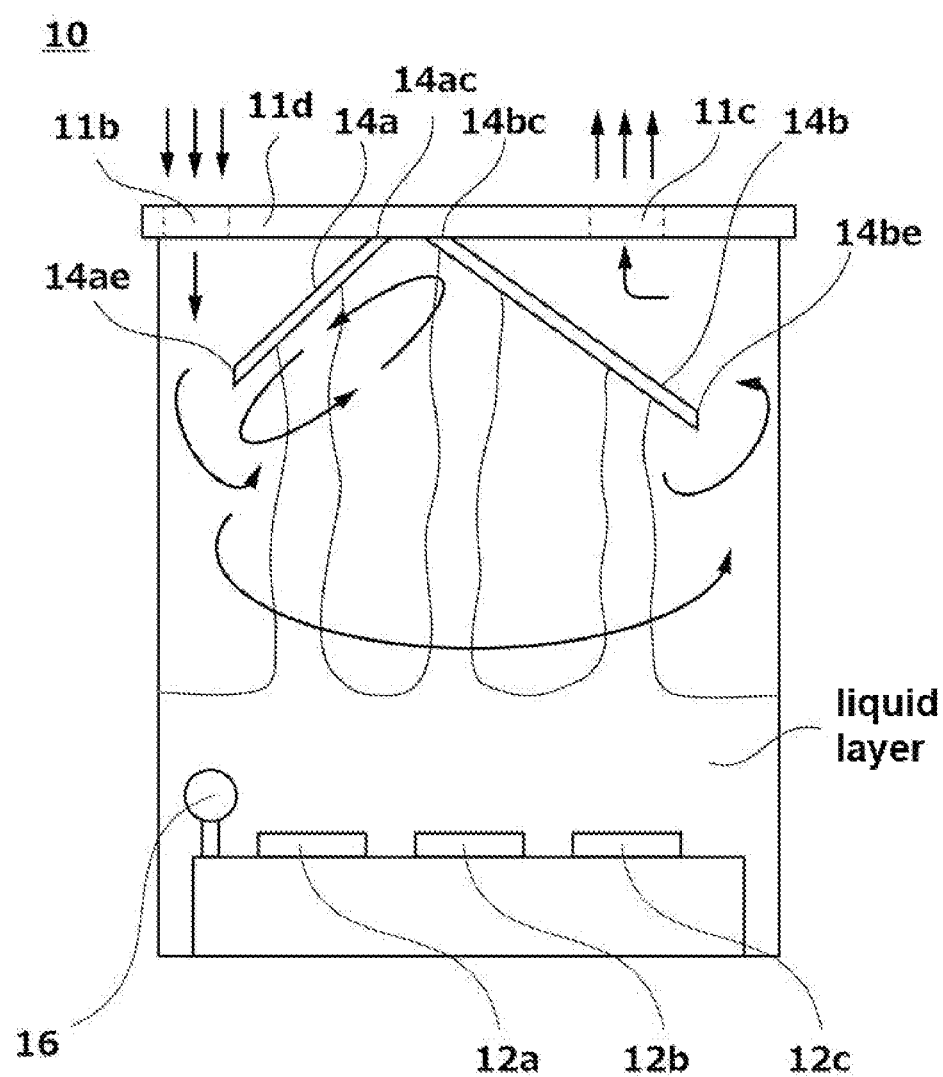
FIG. 7D is a schematic view of the atomization unit 10 involving Modification Example 3, in a state during use.

In particular, as illustrated in FIG. 7A, the baffle plate 14a is drooped perpendicularly downward from the top panel 11d and then inflected horizontally toward the lateral surface along one widthwise end of the atomization tank 11, with the edge piece 14ae disposed spaced apart at a predetermined spacing from the lateral surface along one widthwise end of the atomization tank 11. With this configuration, in the same manner as described above, the conveyance air from the blower 13 can be brought into contact with the surface on one side of the baffle plate 14a to cause pressure loss. As a result, a spraying apparatus 1 can be made available that is capable of conveying only fine particles from the liquid column that has come into contact with the other side of the surface of the baffle plate 14a, and selectively spraying only fine particles that are tiny to a level that can give rise to Brownian motion.

In addition, also with such configuration of the baffle plate 14a, the conveyance air can pass between the edge piece 14ae and the lateral surface along one widthwise end of the atomization tank 11, and pass underneath the baffle plate 14a, and thereby forming a swirling flow in the atomization tank 11 interior. As a result, a spraying apparatus 1 can be made available that is capable of, by exploiting effect of centrifugal separation, conveying only fine particles from the liquid column that has come into contact with the other side of the surface of the baffle plate 14*a*, and selectively spraying only fine particles that are tiny to a level that can give rise to Brownian motion.

Modification 3

The blow port 11*b* and the send-out port 11*c* can be arranged, not in the top panel 11*d* of the atomization tank 11, but in the lateral surface.

As illustrated in FIG. 7B, even in instances in which the blow port 11*b* is arranged in the lateral surface along one widthwise end of the atomization tank 11, as long as it is arranged above the position of the edge piece 14*ae*, because the conveyance air that has flowed in through the blow port 11*b* comes into contact with the baffle plate 14*a*, the pressure loss of the conveyance air is occurred, and the same effect as described above can be obtained.

In addition, as illustrated in FIG. 7C, even in instances in which the send-out port 11*c* is arranged in the lateral surface along the other widthwise end of the atomization tank 11, as long as it is arranged above the position of the edge piece 14*be*, a swirling flow can be formed in the atomization tank 11 interior, and the same effect as described above can be obtained.

In addition, as illustrated in FIG. 7D, the position where the blow port 11*b* is arranged may be arranged in a position with which the conveyance air that has flowed in does not come into contact with the baffle plate 14*a*. Even in such instances, because the conveyance air passes between the lateral surface along one widthwise end of the atomization tank 11 and the edge piece 14*ae* and passes underneath the baffle plate 14*a*, swirling flow can be formed in the atomization tank 11 interior, and the same effect as described above can be obtained.

In this way, baffle plates 14*a* and 14*b* the arrangement or form of which has been changed, or blow port 11*b* and the send-out port 11*c* the arrangement of which has been changed, still fall within the scope of the present invention, as long as the phenomenon described with respect to the present invention can be occurred.

The effects of the present invention described above can be summarized as follows.

Because the baffle plate 14*a* arranged to receive the liquid column of the liquid formulation produced by, among the ultrasonic vibrators, the ultrasonic vibrators 12*a* and 12*d* arranged along one widthwise end, and the baffle plate 14*b* arranged to receive the liquid column of the liquid formulation produced by the ultrasonic vibrators 12*c* and 12*f* arranged along the other widthwise end are provided, the liquid column comes into contact with the baffle plates 14*a* and 14*b* arranged above each of the ultrasonic vibrators 12*a*, 12*b*, 12*c* . . . , liquid droplets of large particle diameter contained in the liquid column comes into contact with the baffle plates 14*a* and 14*b*, flow downward, and flow back to the stored liquid layer, and meanwhile, only large amount of mist droplets of small particle diameter float in the air and are conveyed on the conveyance air.

At this time, the baffle plate 14*a* is furnished with the edge piece 14*ae* disposed spaced apart at a predetermined spacing from the inner face along one widthwise end in the atomization tank 11, and the connection piece 14*ac* connected to the inner side of the atomization tank 11, wherein the blow port 11*b* is arranged more toward one widthwise end of the atomization tank 11 than the connection piece 14*ac* is, and the baffle plate 14*b* is furnished with the edge piece 14*be* disposed spaced apart at a predetermined spacing from the inner face along the other widthwise end in the atomization tank 11, and the connection piece 14*bc* connected to the inner side of the atomization tank 11, wherein the send-out port 11*c* arranged more toward the other widthwise end of the atomization tank 11 than the connection piece 14*bc* is, and thereby, in the atomization tank 11 interior, a large swirling flow is formed over the entire atomization tank 11 with the baffle plate 14*a* and baffle plate 14*b* interposed. Therefore, owing to the centrifugal-force effect that accompanies the production of the swirling flow, minute particles and even more minute fine particles are separated, and a spraying apparatus 1 can be made available that is capable of reliably selecting and spraying a large volume of fine particles that are minute to a level that can give rise to Brownian motion alone.

In addition, since the baffle plate 14*a* is arranged so that the conveyance air supplied through the blow port 11*b* comes into contacts the surface on one side of the baffle plate 14*a*, and therefore on that occasion a pressure loss occurs, with the pressure for conveying the particles dropping. Because the pressure of the conveyance air drops, from the liquid formulation that has been separated into liquid droplets and tiny particles by colliding against the baffle plate 14, only fine particles still smaller than particles of size at the level allowing normal conveyance can be conveyed by the conveyance air.

In addition, because the send-out port 11*c* is arranged on the opposite side from the blow port 11*b* with respect to the connection piece 14*ac* of the baffle plate 14*a*, the conveyance air that comes into contact with the baffle plate 14*a* goes through the spacing formed between the edge piece 14*ae* of the baffle plate 14*a* and the inner face of the atomization tank 11 and arrives at the send-out port 11*c*. On that occasion, a negative pressure region forms along the baffle plate 14*a* on the reverse side of the surface that the conveyance air comes into contact with, that is, the region that the liquid column comes into contact with, and because in the negative-pressure region the pressure of the conveyance air drops still further, particles other than fine particles that are of extraordinarily tiny particle diameter cannot be conveyed, meaning they fall to the liquid surface below. Consequently, fine particles of particle diameter tiny to a level that can give rise to Brownian motion can alone be conveyed toward the send-out port 11*c* by the conveyance air.

In addition, the conveyance air supplied through the blow port 11*b*, after having gone through the spacing formed between the edge piece 14*ae* of the baffle plate 14*a* and the atomization tank 11, winds in on the surface along the liquid-column receiving side, and then arrives at the send-out port 11*c*, surrounding the baffle plate 14*a* gently swirling flow of the conveyance air directed to the send-out port 11*c*. When minute particles separated from the liquid droplets by the collision of the liquid column against the baffle plate 14*a* are carried by the conveyance air, owing to the centrifugal-force effect that accompanies the production of the swirling flow, the minute particles are further separated from even more minute fine particles, and the fine particles alone are conveyed on the conveyance air. Designing in this way affords a spraying apparatus that, thanks to the effect of the baffle plate 14*a* and the effects of the swirling flow, is capable of sending out through the send-out port 11*c* solely fine particles in conjunction with conveyance air.

In addition, because the blow port 11*b* and the send-out port 11*c* are provided on the top panel 11*d* on opposite sides from each other with the baffle plate 14*a* interposed therebetween, a swirling flow in which the baffle plate 14*a* is interposed can be formed, and because the effect of centrifugal separation by the swirling flow can be heightened, a spraying apparatus 1 capable of spraying solely fine particles of tiny diameter can be made available.

In addition, because the baffle plate 14*a* is disposed above the ultrasonic vibrators 12*a* and 12*d* and below the blow port 11*b*, in an orientation blocking liquid columns produced by the ultrasonic vibrators 12*a* and 12*d*, and conveyance air supplied from the blow port 11*b*, the liquid columns produced by the movement of the ultrasonic vibrators 12*a* and 12*d* can be prevented from being blown directly into the blower 13, and meanwhile conveyance air from the blower 13 can be prevented from blowing directly onto the liquid columns. Therefore, a spraying apparatus 1 can be made available that is capable of conveying by means of conveyance air solely minute particles, without spoiling the particle-sorting effect due to the baffle plate 14*a*.

In addition, because in instances in which the liquid level in the atomization tank 11 falls below the predetermined first liquid level h1, supply of the liquid formulation stored in the tank unit 20 is controlled so as to be started, and when the predetermined second level h2 is reached the supply is halted, despite the liquid formulation in the atomization tank 11 interior being consumed as a consequence of an atomization run, the liquid level in the atomization tank 11 interior can be kept between the first liquid level h1 and the second liquid level h2. Accordingly, even in instances in which a large volume of liquid formulation is sprayed over a broad range, the spraying can be stably and automatically continued over a long period of time. And then, because scaling up of the atomization tank 11 can be held back, the capacity of the blower 13 can be made small, affording a spraying apparatus 1 enabling only fine particles of that much tinier particle diameter—that is, only fine particles tiny to a level that can give rise to Brownian motion—to be selected and conveyed.

In addition, because a halt sensor 16 that detects a third liquid level h3 lower than the first liquid level h1 is provided, and the operation of the blower 13 and the atomizing device 12 is halted when the halt sensor 16 senses a fall below the third liquid level h3, on the outside chance that the liquid level falls below the first liquid level h1 and arrives at the third liquid level h3, running of the apparatus on an empty tank can be prevented. Also, since the halt sensor 16 is provided separately from the liquid-level sensor 15, even should the liquid level sensor 15 fail, utilizing of the halt sensor 16 makes it possible to prevent a dangerous empty-tank running state from coming about.

In addition, because the liquid-level sensor 15 is connected to an external part of the atomization tank 11, the influence of local liquid-surface fluctuations in the atomization tank 11 that accompany operation of the ultrasonic vibration elements can be reduced, making it possible to measure accurate liquid levels.

In addition, because the liquid formulation is supplied via the electromagnetic valve from the tank unit 20 arranged above the atomization tank 11, and the liquid formulation can be supplied exploiting gravity, and meanwhile because liquid-formulation supply control can be carried out by only opening-and-closing controlling the electromagnetic valve, a spraying apparatus 1 is afforded that is capable of supplying liquid formulation to the atomization tank 11 more rapidly than by employing the liquid-formulation supply pump 41.

Since the spouting unit 30 is formed by a approximately cylindrical spouting element having predetermined width, depth and height, the generated fine particles are prevented from adhering to the wall surfaces of the spouting element. Further, because a spray port 31 in the form of a slit inclined diagonally upward is furnished along the upper edge of the spouting unit 30, pressure loss during spraying can be controlled to a minimum, wherein even if the pressure for spraying is low, wide-range spraying is possible. Designing in this way affords a spraying apparatus 1 capable of spraying a sufficient volume of fine particles over a broad range even in instances in which the rpm of the blower 13 is low.

In addition, by the atomization tank 11 being anchored to the lower-part base 61, fine particles are produced in the lowest part of the spraying apparatus 1. What is more, by the spouting unit 30 being disposed on the uppermost part upward of the tank unit 20 arranged above the atomization tank 11, the fine particles that are produced ascend from the bottommost part of the apparatus and spout out from the uppermost part. Therefore afforded is a spraying apparatus 1 exploiting the chimney effect to enable the spraying of fine particles over a wide range, even in instances in which the rpm of the blowing element is lowered, lowering the pressure of the blower 13.

The fact that the liquid formulation replenishing port 63*e* for replenishing the tank unit 20 with liquid formulation is furnished in the recess 63*c* provided in the top panel of the top component 63 means that replenishing-supply of liquid formulation from above in a high position in the apparatus is possible, which facilitates replenishing-supply of the liquid formulation. Further, because the liquid-formulation supply port 63*e* is covered by the door-lid 63*d* during the spraying operation, there is no danger of foreign matter entering into the tank unit 20 interior when the door-lid 63*e* is closed, affording, moreover, a spraying apparatus with a neat appearance.

The fact that the periphery of the columnar members 62 is covered with the cover member 80 formed by a stainless-steel sheet affords a spraying apparatus 1 that enables the atomizing unit 10, the tank unit 20, etc. to be covered and concealed from the external environment, and that at the same time gives a sleek impression. In addition, since the cover member is formed by a sheetlike component having elasticity, it can be arranged utilizing the elastic force to wrap it onto the periphery of the columnar members, so that even persons unused to the job can easily attach and detach the cover member 80. Furthermore, the fact that the cover member is strong against corrosion by acids, affords a spraying apparatus 1 that enables the utilization of various liquid formulations, and that can be employed in various environments.

By atomizing the chlorous acid aqueous solution utilizing ultrasonic vibration elements, fine particles tiny to a level that can give rise to Brownian motion can be generated. In addition, because the fine particles generated utilizing the chlorous acid aqueous solution are not prone to becoming deactivated even after a long-term elapse of time, the decontaminating effect can continue over a long period of time. In that situation, the fact that the atomization tank 11 and the tank unit 20 are formed from polyethylene terephthalate, which possesses strong properties against chlorous acid, affords a spraying apparatus 1 that does not require carrying out long-term maintenance, and that is capable of being run continuously. Likewise, because the mounting unit 60 is made of stainless steel, it is not susceptible to corrosion, and the component replacement and the like that is attendant on rusting can be avoided, enabling stabilized running over still longer periods of time.

While the embodying modes of the present invention have been described above, the present invention is not limited to these above-described embodying modes. Furthermore, the effects described in embodying modes of the present invention are merely listing of most favorable effects that arise from the present invention; the effects of the present invention are not limited to those described in the embodying modes of the present invention.

In addition, the above-described embodying modes are described in detail for the purpose of explaining the present invention for comprehensibility, and are not necessarily limited to those with all of the described configurations.

INDUSTRIAL EXPLOITABILITY

The spraying apparatus of the present invention can be applicable to various spraying devices that spray various types of liquids.

Appended Text 1

A spraying device 1 of Appended Text 1 is as follows.

TECHNICAL FIELD

The present invention relates to technology for generating fine particles in a spraying device that sprays liquid into a space.

BACKGROUND ART

Various spraying devices that atomize and spray into a space water or aqueous solutions that exhibit predetermined effects have been developed.

In spraying devices of this kind, in order to uniformly and wide-rangingly diffuse fine particles inside a space, it is necessary to stably generate fine particles having a desired particle size—in particular, a particle size tiny to a level at which the fine particles can give rise to Brownian motion within air.

As an example of this sort of spraying device, there is the instance in which, e.g., in a broad space such as an elderly-facility assembly hall, or livestock shelter such as a cowshed, piggery, or poultry farm, the need arises to spray a large volume of a liquid formulation having a disinfecting action. In such instances, it is undesirable that the particle diameters be large, because the particles will fall to the floor or ground before reaching every nook and cranny of the space, and at the same time dampen the floor, walls, and skin, becoming the cause of slipping, of mold and mildew, and of colds. Therefore, in order that the particles float within the air for a long time such that the sterilizing effectiveness is demonstrated, it is necessary to generate fine particles having particle diameters tiny to a level that can give rise to Brownian motion.

In general, in order to atomize and spray a liquid, in an atomization unit in which water or an aqueous solution is stored, technology is adopted in which a liquid column generated utilizing a vibrator such as an ultrasonic vibrator is collided against a separator and separated into large liquid droplets and small mist droplets, and a conveyance medium supplied from a blower or the like is utilized to convey and diffuse into the air the mist droplets alone. (JP H8-309248 A, JP S60-50728 U)

SUMMARY OF INVENTION

Issues Invention is to Address

The technology disclosed in JP H8-309248 A and JP S60-50728 U affords a spray apparatus capable of selectively spraying mist droplets separated from liquid droplets. Nevertheless, with the technology disclosed in JP H8-309248 A and JP S60-50728 U, because air is directly supplied to the region where the liquid column collides on the separator, due to the air the flow is disturbed, such that particles of relatively large particle diameter also get swept into and are conveyed on the air. Consequently, the particle diameter of fine particles conveyed on the air and sprayed is on the order of 10 μm, encumbering the generating of fine particles (particle size of about 0.1 to 2 μm) that are tiny to a level that can give rise to Brownian motion.

What is more, in order to evenly spread fine particles over a broad space, it is necessary to supply a large volume of conveyance air for conveying the fine particles, meaning that in such cases not only fine particles of tiny diameter but also particles whose diameter is large are conveyed, making difficult the conveying of only fine particles that are tiny to a level that can give rise to Brownian motion.

Generating/conveying only tiny fine particles necessitates controlling with high precision the voltage applied to the vibration elements and the rpm of the delivery machine at the same time, which without specialized knowledge is challenging.

An object of the present invention, brought about taking these sorts of issues into consideration, is to make available a spraying apparatus that, even for persons for whom the job is unfamiliar, is capable of generating a large volume of fine particles having particle diameters minute to a level that stably can give rise to Brownian motion, even without complex control employing expensive control devices.

Means for Resolving Issues

The present invention makes available the following sort of resolution means.

The invention involving a first characteristic affords a spraying apparatus provided with: an atomization tank enabled for storing a liquid formulation; an atomizing device being an ultrasound vibrating element arranged in the atomization tank interior, for atomizing the liquid formulation to generate fine particles; a blower furnished with a blowing element enabled for maintaining predetermined rpm, for blasting into the atomization tank interior, through a blow port provided in the atomization tank, conveyance air that is for conveying the fine particles of the liquid formulation; a baffle plate arranged in the atomization tank interior; wherein with one end part of the baffle plate being spaced apart at a predetermined spacing from the inner surface of the atomization tank, the other end part is connected to the inner side of the atomization tank, and meanwhile the baffle plate is arranged so as to receive, at a surface on one side thereof, conveyance air through the blow port, and to receive, at a surface on the other side thereof, liquid columns of the liquid formulation, generated by the ultrasonic vibration elements.

According to the invention involving the first characteristic, since the conveyance air supplied from the blower port contacts the surface on one side along the baffle plate, on that occasion a pressure loss occurs, with the pressure for conveying the particles dropping. Because the pressure of the conveyance air drops, from the liquid formulation that has been separated into liquid droplets and tiny particles by colliding against the baffle plate, only fine particles still smaller than particles of size at the level allowing normal conveyance are conveyed by the conveyance air.

The invention involving a second characteristic is the invention involving the first characteristic, while affording a spray apparatus wherein the send-out port is arranged in a position on a opposite side with respect to the connection piece on the baffle plate from the position where the blow port is arranged.

According to the invention involving the second characteristic, because the send-out port is arranged on the opposite side from the blow port with respect to the connection piece on the baffle plate, the conveyance air that comes into contact with the baffle plate goes through the spacing formed between the one end of the baffle plate and the inner face of the atomization tank and arrives at the send-out port. On that occasion, a negative pressure region forms along the baffle plate on the reverse side of the surface that the conveyance air comes into contact with, that is, the region that the liquid column comes into contact with, and because in the negative pressure region the pressure of the conveyance air drops still further, particles apart from fine particles that are of extraordinarily tiny particle diameter cannot be conveyed, meaning they fall to the liquid surface below. Consequently, fine particles of particle diameter tiny to a level that can give rise to Brownian motion can alone be conveyed toward the send-out port by the conveyance air.

Designing in this way affords a spraying apparatus that, more than simply receiving liquid columns at the baffle plate makes possible conveying minute particles by means of conveyance air, and enables the selective spraying of only fine particles that are tiny to a level that can give rise to Brownian motion.

The invention involving a third characteristic makes available a spraying method having a step of contacting conveyance air on the upper surface of a baffle plate projecting laterally or diagonally downward, a step of colliding against a lower surface of the baffle plate a liquid column of a liquid formulation produced by ultrasonic vibration elements, a step of causing conveyance air having been made to collide with the upper surface of the baffle plate to flow along the lower surface of the baffle plate, and a step of sending out the conveyance air.

According to the invention involving the third characteristic, bringing the conveyance air into contact with the upper surface of the baffle plate and then causing it to flow on the lower surface of the baffle plate causes the conveyance air, in a state in which it has been caused to produce a pressure loss, to convey particles atomized from the liquid column. The fact that conveyance air whose pressure has dropped is utilized to convey particles enables making available a spray apparatus capable of separating and conveying only fine particles of especially tiny particle diameter. Therefore, even with a relatively large flow volume being secured, a spraying method is afforded that is capable of conveying and spraying only particles of especially tine particle diameter.

The invention involving a fourth characteristic is the invention involving the third characteristic, while further having a step of controlling the rpm of a blowing element for supplying conveyance air.

According to the invention involving the fourth characteristic, by controlling the rpm of the blowing element in a state in which pressure loss in the conveyance air has been brought about, change in air pressure with respect to change in conveyance-air fanning volume can be made larger, affording a spraying method capable of changing particle diameter without changing spray volume.

Appended Text 2

A spraying device 1 of Appended Text 2 is as follows.

TECHNICAL FIELD

The present invention relates to technology for generating fine particles in a spraying device that sprays liquid into a space.

BACKGROUND ART

Various spraying devices that atomize and spray into a space water or aqueous solutions that exhibit predetermined effects have been developed.

In spraying devices of this kind, in order to uniformly and wide-rangingly diffuse fine particles inside a space, it is necessary to stably generate fine particles having a desired particle size—in particular, a particle size tiny to a level at which the fine particles can give rise to Brownian motion within air.

As an example of this sort of spraying device, there is the instance in which, e.g., in a broad space such as an elderly-facility assembly hall, or livestock shelter such as a cowshed, piggery, or poultry farm, the need arises to spray a large volume of a liquid formulation having a disinfecting action. In such instances, it is undesirable that the particle diameters be large, because the particles will fall to the floor or ground before reaching every nook and cranny of the space, and at the same time dampen the floor, walls, and skin, becoming the cause of slipping, of mold and mildew, and of colds. Therefore, in order that the particles float within the air for a long time such that the sterilizing effectiveness is demonstrated, it is necessary to generate fine particles having particle diameters tiny to a level that can give rise to Brownian motion.

In general, in order to atomize and spray a liquid, in an atomization unit in which water or an aqueous solution is stored, technology is adopted in which a liquid column generated utilizing a vibrator such as an ultrasonic vibrator is collided against a separator and separated into large liquid droplets and small mist droplets, and a conveyance medium supplied from a blower or the like is utilized to convey and diffuse into the air the mist droplets alone. (JP H8-309248 A, JP S60-50728 U)

SUMMARY OF INVENTION

Issues Invention is to Address

The technology disclosed in JP H8-309248 A and JP S60-50728 U affords a spray apparatus capable of selectively spraying mist droplets separated from liquid droplets. Nevertheless, with the technology disclosed in JP H8-309248 A and JP S60-50728 U, because air is directly supplied to the region where the liquid column collides on the separator, due to the air the flow is disturbed, such that particles of relatively large particle diameter also get swept into and are conveyed on the air. Consequently, the particle diameter of fine particles conveyed on the air and sprayed is on the order of 10 μm, encumbering the generating of fine particles (particle size of about 0.1 to 2 μm) that are tiny to a level that can give rise to Brownian motion.

What is more, in order to evenly spread fine particles over a broad space, it is necessary to supply a large volume of conveyance air for conveying the fine particles, meaning that in such cases not only fine particles of tiny diameter but also particles whose diameter is large are conveyed, making difficult the conveying of only fine particles that are tiny to a level that can give rise to Brownian motion.

Generating/conveying only tiny fine particles necessitates controlling with high precision the voltage applied to the vibration elements and the rpm of the delivery machine at the same time, which without specialized knowledge is challenging.

An object of the present invention, brought about taking these sorts of issues into consideration, is to make available a spraying apparatus that, even for persons for whom the job is unfamiliar, is capable of generating a large volume of fine particles having particle diameters minute to a level that stably can give rise to Brownian motion, even without complex control employing expensive control devices.

Means for Resolving Issues

The present invention makes available the following sort of resolution means.

The invention involving a first characteristic affords a spraying apparatus provided with: an atomization tank enabled for storing a liquid formulation; an atomizing device being an ultrasound vibrating element arranged in the atomization tank interior, for atomizing the liquid formulation to generate fine particles; a blower furnished with a blowing element enabled for maintaining predetermined rpm, for blasting into the atomization tank interior, through a blow port provided in the atomization tank, conveyance air that is for conveying the fine particles of the liquid formulation; a send-out port, provided in the atomization tank, through which the fine particles are sent out together with the conveyance air; and a baffle plate arranged in the atomization tank so as to receive liquid columns of the liquid formulation, generated by the ultrasonic vibration elements; wherein the spacing and the send-out port are disposed so that conveyance air supplied through the blow port goes through a spacing between one end part of the baffle plate and the atomization tank, winds in along the surface on the plate's liquid-column receiving side and then arrives at the send-out port.

According to the invention involving the first characteristic, because the conveyance air supplied from the blower port, after having gone through the spacing formed between the one end part of the baffle plate and the atomization tank, winds in on the surface along the liquid-column receiving side and then arrives at the send-out port, surrounding the baffle plate a gently swirling flow of the conveyance air directed to the send-out port is formed. Minute particles separated from the liquid droplets by the collision of the liquid column against the baffle plate are carried by the conveyance air, and in that situation, owing to the centrifugal-force effect that accompanies the production of the swirling flow, the minute particles are further separated from even more minute fine particles, and the fine particles alone are conveyed on the conveyance air. Designing in this way affords a spraying apparatus that, thanks to the baffle plate's effect and the effects of the swirling flow, is capable of sending out through the send-out port solely fine particles in conjunction with conveyance air.

The invention involving a second characteristic is the invention involving the first characteristic, while affording a spraying apparatus wherein an end part of the baffle plate is connected to the inner side of a top panel of the atomization tank, and the blow port and the send-out port are provided on the top panel of the atomization tank and in locations on opposite sides from each other, with the baffle plate being put in between.

According to the invention involving the second characteristic, because the blow port and the send-out port are provided on the top panel on opposite sides from each other with the baffle plate interposed therebetween, a swirling flow in which the baffle plate is interposed can be formed, and because the effect of centrifugal separation by the swirling flow can be heightened, a spraying apparatus capable of spraying soley fine particles of tiny particle diameter can be made available.

The invention involving a third characteristic makes available a spraying method having a step of producing a down-directed conveyance-air flow in an atomization tank interior to produce a swirling flow of the conveyance air in the entirety of the atomization tank interior; a step of contacting a lower surface of a baffle plate with a liquid-formulation liquid column having been produced by ultrasonic vibration element; a step of causing a swirl flow to flow on the lower surface of the baffle plate; and a step of sending out the swirl flow from above by means of conveyance air.

According to the invention involving the third characteristic, a spraying method is afforded that by producing a swirling flow of conveyance air throughout the entire atomization tank, and utilizing the centrifugal force of the swirling flow to separate particles of tiny particle size produced by contacting on the baffle plate a liquid column due to the agency of ultrasonic vibration elements enables picking out solely fine particles that are still tinier.

The invention involving a fourth characteristic is the invention involving the third characteristic, further having a step of controlling the rpm of the blowing element for supplying the conveyance air.

According to the invention involving the fourth characteristic, a spraying method is afforded that by controlling the rpm of the blowing element, enables the swirling strength of the swirling flow to be controlled, whereby change in conveying capacity of the conveyance air with respect to change in its fanning volume can be made larger, making it possible to change the particle size without changing the spraying volume.

Appended Text 3

A spraying device 1 of Appended Text 3 is as follows.

TECHNICAL FIELD

The present invention relates to technology for generating fine particles in a spraying device that sprays liquid into a space.

BACKGROUND ART

Various spraying devices that atomize and spray into a space water or aqueous solutions that exhibit predetermined effects have been developed.

In spraying devices of this kind, in order to uniformly and wide-rangingly diffuse fine particles inside a space, it is necessary to stably generate fine particles having a desired particle size—in particular, a particle size tiny to a level at which the fine particles can give rise to Brownian motion within air.

As an example of this sort of spraying device, there is the instance in which, e.g., in a broad space such as an elderly-facility assembly hall, or livestock shelter such as a cow-shed, piggery, or poultry farm, the need arises to spray a large volume of a liquid formulation having a disinfecting action. In such instances, it is undesirable that the particle diameters be large, because the particles will fall to the floor or ground before reaching every nook and cranny of the space, and at the same time dampen the floor, walls, and skin, becoming the cause of slipping, of mold and mildew, and of colds. Therefore, in order that the particles float within the air for a long time such that the sterilizing effectiveness is demonstrated, it is necessary to generate fine particles having particle diameters tiny to a level that can give rise to Brownian motion.

In general, in order to atomize and spray a liquid, in an atomization unit in which water or an aqueous solution is stored, technology is adopted in which a liquid column generated utilizing a vibrator such as an ultrasonic vibrator is collided against a separator and separated into large liquid droplets and small mist droplets, and a conveyance medium supplied from a blower or the like is utilized to convey and diffuse into the air the mist droplets alone. (JP H8-309248 A, JP S60-50728 U)

SUMMARY OF INVENTION

Issues Invention is to Address

The technology disclosed in JP H8-309248 A and JP S60-50728 U affords a spray apparatus capable of selectively spraying mist droplets separated from liquid droplets. Nevertheless, with the technology disclosed in JP H8-309248 A and JP S60-50728 U, because air is directly supplied to the region where the liquid column collides on the separator, due to the air the flow is disturbed, such that particles of relatively large particle diameter also get swept into and are conveyed on the air. Consequently, the particle diameter of fine particles conveyed on the air and sprayed is on the order of 10 μm, encumbering the generating of fine particles (particle size of about 0.1 to 2 μm) that are tiny to a level that can give rise to Brownian motion.

What is more, in order to evenly spread fine particles over a broad space, it is necessary to supply a large volume of conveyance air for conveying the fine particles, meaning that in such cases not only fine particles of tiny diameter but also particles whose diameter is large are conveyed, making difficult the conveying of only fine particles that are tiny to a level that can give rise to Brownian motion.

Generating/conveying only tiny fine particles necessitates controlling with high precision the voltage applied to the vibration elements and the rpm of the delivery machine at the same time, which without specialized knowledge is challenging.

An object of the present invention, brought about taking these sorts of issues into consideration, is to make available a spraying apparatus that, even for persons for whom the job is unfamiliar, is capable of generating a large volume of fine particles having particle diameters minute to a level that stably can give rise to Brownian motion, even without complex control employing expensive control devices.

Means for Resolving Issues

The present invention makes available the following sort of resolution means.

The invention involving a first characteristic affords a spraying apparatus provided with: an atomization tank enabled for storing a liquid formulation; an atomizing device being an ultrasound vibrating element arranged in the atomization tank interior, for atomizing the liquid formulation to generate fine particles; a blower furnished with a blowing element enabled for maintaining predetermined rpm, for blasting into the atomization tank interior, through a blow port provided in a top panel of the atomization tank, conveyance air that is for conveying the fine particles of the liquid formulation; a send-out port, provided in the atomization tank, through which the fine particles are sent out together with the conveyance air; and a baffle plate arranged in the atomization tank; wherein the baffle plate is disposed above the ultrasonic vibration elements, and underneath the blow port, in an orientation blocking liquid columns produced by the ultrasonic vibration elements, and conveyance air supplied from the blow port.

According to the invention involving the first characteristic, because the baffle plate is disposed above the ultrasonic vibration elements and below the blow port, in an orientation blocking liquid columns produced by the ultrasonic vibration elements, and conveyance air supplied from the blow port, the liquid columns produced by the movement of the ultrasonic vibration elements can be prevented from being blown directly into the blower, and meanwhile conveyance air from the blower can be prevented from blowing directly onto the liquid columns. Therefore, a spraying apparatus can be made available that is capable of conveying by means of conveyance air solely minute particles, without spoiling the particle-sorting effect due to the baffle plate.

Appended Text 4

A spraying device 1 of Appended Text 4 is as follows.

TECHNICAL FIELD

The present invention relates to technology for generating fine particles in a spraying device that sprays liquid into a space.

BACKGROUND ART

Various spraying devices that atomize and spray into a space water or aqueous solutions that exhibit predetermined effects have been developed.

In spraying devices of this kind, in order to uniformly and wide-rangingly diffuse fine particles inside a space, it is necessary to stably generate fine particles having a desired particle size—in particular, a particle size tiny to a level at which the fine particles can give rise to Brownian motion within air.

As an example of this sort of spraying device, there is the instance in which, e.g., in a broad space such as an elderly-facility assembly hall, or livestock shelter such as a cow-shed, piggery, or poultry farm, the need arises to spray a large volume of a liquid formulation having a disinfecting action. In such instances, it is undesirable that the particle diameters be large, because the particles will fall to the floor or ground before reaching every nook and cranny of the space, and at the same time dampen the floor, walls, and skin, becoming the cause of slipping, of mold and mildew, and of colds. Therefore, in order that the particles float within the air for a long time such that the sterilizing effectiveness is demonstrated, it is necessary to generate fine particles having particle diameters tiny to a level that can give rise to Brownian motion.

In general, in order to atomize and spray a liquid, in an atomization unit in which water or an aqueous solution is stored, technology is adopted in which a liquid column generated utilizing a vibrator such as an ultrasonic vibrator is collided against a separator and separated into large liquid droplets and small mist droplets, and a conveyance medium supplied from a blower or the like is utilized to convey and diffuse into the air the mist droplets alone. (JP H8-309248 A, JP S60-50728 U)

SUMMARY OF INVENTION

Issues Invention is to Address

The technology disclosed in JP H8-309248 A and JP S60-50728 U affords a spray apparatus capable of selectively spraying mist droplets separated from liquid droplets. Nevertheless, with the technology disclosed in JP H8-309248 A and JP S60-50728 U, because air is directly supplied to the region where the liquid column collides on the separator, due to the air the flow is disturbed, such that particles of relatively large particle diameter also get swept into and are conveyed on the air. Consequently, the particle diameter of fine particles conveyed on the air and sprayed is on the order of 10 µm, encumbering the generating of fine particles (particle size of about 0.1 to 2 µm) that are tiny to a level that can give rise to Brownian motion.

In addition, in order to continue the operation of spreading fine particles evenly over a wide space, the atomization tank equipped with an ultrasonic vibrator is enlarged, and a large amount of liquid formulation is generated by using multiple ultrasonic vibrators. It was necessary to atomize the fine particles and convey the fine particles using a large amount of conveyance air. In this case, it turns out that not only fine particles of tiny particle diameter, but also particles of large particle diameter are conveyed by the large volume of conveyance air, encumbering the conveying of solely fine particles tiny to a level that can give rise to Brownian motion.

Generating/conveying only tiny fine particles necessitates controlling simultaneously and with high precision the voltage applied to the vibration elements and the rpm of the delivery machine, which without specialized knowledge is challenging.

An object of the present invention, brought about taking these sorts of issues into consideration, is to make available a spraying apparatus that, even for persons for whom the job is unfamiliar, is capable of continuing over a long time period stable and automatic spraying over a broad range of a large volume of liquid formulation, and that is capable of large-volume generating fine particles having particle diameters minute to a level that that can stably give rise to Brownian motion, even without complex control employing expensive control devices.

Means for Resolving Issues

The present invention makes available the following sort of resolution means.

An invention involving a first characteristic comprises: an atomization unit furnished with an atomization tank enabled for storing a liquid formulation, an atomizing device for atomizing the liquid formulation in the atomization tank to generate fine particles, and a blower furnished with a blowing element enabled for maintaining predetermined rpm, for blasting into the atomization tank interior, through a blow port provided in the atomization tank, conveyance air that is for conveying the fine particles of the liquid formulation, a liquid-level sensor for measuring fluid level in the atomization tank; a tank unit for supplying the liquid formulation to the atomization tank; and a control unit for controlling supply of the liquid formulation from the tank unit to the atomization tank; wherein the control unit, when the liquid level measured by the liquid-level sensor falls below a predetermined first level, starts supply of the liquid formulation from the tank unit to the atomization tank, and when the liquid level measured by the liquid-level sensor reaches a predetermined second level higher than the first level, halts supply of the liquid formulation from the tank unit to the atomization tank.

According to the invention involving the first characteristic, because in instances in which the liquid level in the atomization tank falls below the predetermined first level supply of the liquid formulation stored in the tank unit is controlled so as to be started, and when the predetermined second level is reached the supply is halted, despite the liquid formulation in the atomization tank interior being consumed as a consequence of an atomization run, the liquid level in the atomization tank interior can be kept between the first liquid level and the second liquid level. Accordingly, even in instances in which a large volume of liquid formulation is sprayed over a broad range, the spraying can be stably and automatically continued over a long period of time. And then, because scaling up of the atomization tank can be held back, the blower capacity can be made small, affording a spraying apparatus enabling only fine particles of that much tinier particle diameter—that is, only fine particles tiny to a level that can give rise to Brownian motion—to be selected and conveyed.

The invention involving a second characteristic is the invention involving the first characteristic, and making available a spraying apparatus wherein the control unit is further enabled for controlling the operation of the atomization device and the operation of the blower, and the atomization tank is further furnished with a halt sensor for sensing a predetermined third liquid level lower than the first level, and the control unit, if the halt sensor senses a fall below the third liquid level, halts operation of the blower and operation of the atomization device.

According to the invention involving the second characteristic, because the operation of the blower and the atomization device is halted when a fall below the third liquid level is sensed, on the outside chance that the liquid level falls below the first level and arrives at the third level, running of the apparatus on an empty tank can be prevented. Also, since the halt sensor is provided separately from the liquid-level sensor, even should the liquid level sensor fail, utilizing of the stop sensor makes it possible to prevent a dangerous empty-tank running state from coming about.

The invention involving a third characteristic is the invention according to the first or second characteristic, and making available a spraying apparatus wherein the liquid-level sensor is a float level sensor connected to an external part of the atomization tank.

According to the invention involving the third characteristic, because the liquid-level sensor for measuring liquid level is connected to an external part of the atomization tank, the influence of local liquid-surface fluctuations in the atomization tank that accompany operation of the ultrasonic vibration elements can be reduced, making it possible to measure accurate liquid levels.

Appended Text 5

A spraying device 1 of Appended Text 5 is as follows.

TECHNICAL FIELD

The present invention relates to technology for generating fine particles in a spraying device that sprays liquid into a space.

BACKGROUND ART

Various spraying devices that atomize and spray into a space water or aqueous solutions that exhibit predetermined effects have been developed.

In spraying devices of this kind, in order to uniformly and wide-rangingly diffuse fine particles inside a space, it is necessary to stably generate fine particles having a desired particle size—in particular, a particle size tiny to a level at which the fine particles can give rise to Brownian motion within air.

As an example of this sort of spraying device, there is the instance in which, e.g., in a broad space such as an elderly-facility assembly hall, or livestock shelter such as a cow-shed, piggery, or poultry farm, the need arises to spray a large volume of a liquid formulation having a disinfecting action. In such instances, it is undesirable that the particle diameters be large, because the particles will fall to the floor or ground before reaching every nook and cranny of the space, and at the same time dampen the floor, walls, and skin, becoming the cause of slipping, of mold and mildew, and of colds. Therefore, in order that the particles float within the air for a long time such that the sterilizing effectiveness is demonstrated, it is necessary to generate fine particles having particle diameters tiny to a level that can give rise to Brownian motion.

In general, in order to atomize and spray a liquid, in an atomization unit in which water or an aqueous solution is stored, technology is adopted in which a liquid column generated utilizing a vibrator such as an ultrasonic vibrator is collided against a separator and separated into large liquid droplets and small mist droplets, and a conveyance medium supplied from a blower or the like is utilized to convey and diffuse into the air the mist droplets alone. (JP H8-309248 A, JP S60-50728 U)

SUMMARY OF INVENTION

Issues Invention is to Address

The technology disclosed in JP H8-309248 A and JP S60-50728 U affords a spray apparatus capable of selectively spraying mist droplets separated from liquid droplets. Nevertheless, with the technology disclosed in JP H8-309248 A and JP S60-50728 U, because air is directly supplied to the region where the liquid column collides on the separator, due to the air the flow is disturbed, such that particles of relatively large particle diameter also get swept into and are conveyed on the air. Consequently, the particle diameter of fine particles conveyed on the air and sprayed is on the order of 10 μm, encumbering the generating of fine particles (particle size of about 0.1 to 2 μm) that are tiny to a level that can give rise to Brownian motion.

What is more, in order to carry out operational running that spreads fine particles evenly over a broad space, in the first place, it is necessary that start-up of the spray apparatus takes place swiftly, wherein when the spraying apparatus is being started up, the liquid formulation must be supplied swiftly into the atomization tank furnished with the ultrasonic vibration elements. In that situation, if the atomization tank is large-scale, because supplying it with liquid formulation would take time, time until start-up would also be taken.

An object of the present invention, brought about taking these sorts of issues into consideration, is to make available, in spraying apparatuses capable of generating a large volume of fine particles having particle diameters minute to a level that can stably give rise to Brownian motion, a spraying apparatus with which start-up is carried out swiftly, and that is capable of spraying over a long period of time a large volume of liquid formulation stably over a broad range.

Means for Resolving Issues

The present invention makes available the following sort of resolution means.

The invention involving a first characteristic makes available a spraying apparatus comprising: an atomization unit furnished with an atomization tank enabled for storing a liquid formulation, an atomizing device for atomizing the liquid formulation in the atomization tank interior to generate fine particles, and a blower for producing conveyance air that carries the fine particles of the liquid formulation; a tank unit arranged above the atomization unit, for supplying liquid formulation to the atomization tank; and a control unit for controlling supply of the liquid formulation from the tank unit to the atomization tank; the spraying apparatus being wherein the atomization unit and the tank unit are connected via an electromagnetic valve, and the control unit supplies the liquid formulation from the tank unit to the atomization tank by opening and closing the electromagnetic valve. for controlling the According to the invention involving the first characteristic, because the liquid formulation is supplied via the solenoid valve from the tank unit arranged above the atomization tank, the liquid formulation can be supplied exploiting gravity, and meanwhile because liquid-formulation supply control can be carried out by only opening-and-closing controlling the electromagnetic valve, a spraying apparatus is afforded that is capable of supplying liquid formulation to the atomization tank more rapidly than by employing a pump.

Appended Text 6

A spraying device 1 of Appended Text 6 is as follows.

TECHNICAL FIELD

TECHNICAL FIELD

The present invention relates to technology for generating fine particles in a spraying device that sprays liquid into a space.

BACKGROUND ART

Various spraying devices that atomize and spray into a space water or aqueous solutions that exhibit predetermined effects have been developed.

In spraying devices of this kind, in order to uniformly and wide-rangingly diffuse fine particles inside a space, it is necessary to stably generate fine particles having a desired particle size—in particular, a particle size tiny to a level at which the fine particles can give rise to Brownian motion within air.

As an example of this sort of spraying device, there is the instance in which, e.g., in a broad space such as an elderly-facility assembly hall, or livestock shelter such as a cowshed, piggery, or poultry farm, the need arises to spray a large volume of a liquid formulation having a disinfecting action. In such instances, it is undesirable that the particle diameters be large, because the particles will fall to the floor or ground before reaching every nook and cranny of the space, and at the same time dampen the floor, walls, and skin, becoming the cause of slipping, of mold and mildew, and of colds. Therefore, in order that the particles float within the air for a long time such that the sterilizing effectiveness is demonstrated, it is necessary to generate fine particles having particle diameters tiny to a level that can give rise to Brownian motion.

In general, in order to atomize and spray a liquid, in an atomization unit in which water or an aqueous solution is stored, technology is adopted in which a liquid column generated utilizing a vibrator such as an ultrasonic vibrator is collided against a separator and separated into large liquid droplets and small mist droplets, and a conveyance medium supplied from a blower or the like is utilized to convey and diffuse into the air the mist droplets alone. (JP H8-309248 A, JP S60-50728 U)

SUMMARY OF INVENTION

Issues Invention is to Address

The technology disclosed in JP H8-309248 A and JP S60-50728 U affords a spray apparatus capable of selectively spraying mist droplets separated from liquid droplets. Nevertheless, with the technology disclosed in JP H8-309248 A and JP S60-50728 U, because air is directly supplied to the region where the liquid column collides on the separator, due to the air the flow is disturbed, such that particles of relatively large particle diameter also get swept into and are conveyed on the air. Consequently, the particle diameter of fine particles conveyed on the air and sprayed is on the order of 10 µm, encumbering the generating of fine particles (particle size of about 0.1 to 2 µm) that are tiny to a level that can give rise to Brownian motion.

What is more, in order to evenly spread fine particles over a broad space, it is necessary to supply a large volume of conveyance air for conveying the fine particles, meaning that in such cases not only fine particles of tiny diameter but also particles whose diameter is large are conveyed, making difficult the conveying of only fine particles that are tiny to a level that can give rise to Brownian motion.

Generating/conveying only tiny fine particles necessitates controlling with high precision the voltage applied to the vibration elements and the rpm of the delivery machine at the same time, which without specialized knowledge is challenging.

In particular, selectively producing fine particles of tiny particle diameter requires lowering the rpm of the blower. Lowering the rpm of the blower enables making it so that air drafts are lowered and large, heavy particles are not conveyed, therefore making it possible to selectively convey fine particles of tiny particle diameter. If, however, the rpm of the blower is lowered, because the fanning volume goes down at the same time, spraying across wide areas is impossible, making the spraying of assembly halls, livestock sheds, etc. challenging.

An object of the present invention, brought about taking these sorts of issues into consideration, is to make available a spraying apparatus that, even for persons for whom the job is unfamiliar, is capable of generating a large volume of fine particles having particle diameters minute to a level that stably can give rise to Brownian motion, even without complex control employing expensive control devices.

Means for Resolving Issues

The present invention makes available the following sort of resolution means.

The invention involving a first characteristic makes available a spraying apparatus comprising: an atomization unit furnished with an atomization tank enabled for storing a liquid formulation, an atomizing device for atomizing the liquid formulation in the atomization tank interior to generate fine particles, and a blower furnished with a blowing element enabled for maintaining predetermined rpm, for blasting into the atomization tank interior, through a blow port provided in the atomization tank, conveyance air that is for conveying the fine particles of the liquid formulation; and a spouting unit for spouting out together with conveyance air the fine particles generated by the atomization unit; the spraying apparatus being wherein the spouting unit is formed by an approximately cylindrical spouting element having predetermined width, depth and height, and having a spray port in the form of a slit inclined diagonally upward at the upper edge.

According to the invention involving the first characteristic, since the spouting unit is formed by a approximately cylindrical spouting element having predetermined width, depth and height, the generated fine particles are prevented from adhering to the wall surfaces. Further, because a spray port in the form of a slit inclined diagonally upward is furnished along the upper edge of the spouting unit, pressure loss during spraying can be controlled to a minimum, wherein even if the pressure for spraying is low, wide-range spraying is possible. Designing in this way affords a spraying apparatus capable of spraying a sufficient volume of fine particles over a broad range even in instances in which the rpm of the blower is low.

Appended Text 7

A spraying device 1 of Appended Text 7 is as follows.

TECHNICAL FIELD

The present invention relates to technology for generating fine particles in a spraying device that sprays liquid into a space.

BACKGROUND ART

Various spraying devices that atomize and spray into a space water or aqueous solutions that exhibit predetermined effects have been developed.

In spraying devices of this kind, in order to uniformly and wide-rangingly diffuse fine particles inside a space, it is necessary to stably generate fine particles having a desired particle size—in particular, a particle size tiny to a level at which the fine particles can give rise to Brownian motion within air.

As an example of this sort of spraying device, there is the instance in which, e.g., in a broad space such as an elderly-facility assembly hall, or livestock shelter such as a cow-shed, piggery, or poultry farm, the need arises to spray a large volume of a liquid formulation having a disinfecting action. In such instances, it is undesirable that the particle diameters be large, because the particles will fall to the floor or ground before reaching every nook and cranny of the space, and at the same time dampen the floor, walls, and skin, becoming the cause of slipping, of mold and mildew, and of colds. Therefore, in order that the particles float within the air for a long time such that the sterilizing effectiveness is demonstrated, it is necessary to generate fine particles having particle diameters tiny to a level that can give rise to Brownian motion.

In general, in order to atomize and spray a liquid, in an atomization unit in which water or an aqueous solution is stored, technology is adopted in which a liquid column generated utilizing a vibrator such as an ultrasonic vibrator is collided against a separator and separated into large liquid droplets and small mist droplets, and a conveyance medium supplied from a blower or the like is utilized to convey and diffuse into the air the mist droplets alone. (JP H8-309248 A, JP S60-50728 U)

SUMMARY OF INVENTION

Issues Invention is to Address

The technology disclosed in JP H8-309248 A and JP S60-50728 U affords a spray apparatus capable of selectively spraying mist droplets separated from liquid droplets. Nevertheless, with the technology disclosed in JP H8-309248 A and JP S60-50728 U, because air is directly supplied to the region where the liquid column collides on the separator, due to the air the flow is disturbed, such that particles of relatively large particle diameter also get swept into and are conveyed on the air. Consequently, the particle diameter of fine particles conveyed on the air and sprayed is on the order of 10 μm, encumbering the generating of fine particles (particle size of about 0.1 to 2 μm) that are tiny to a level that can give rise to Brownian motion.

What is more, in order to evenly spread fine particles over a broad space, it is necessary to supply a large volume of conveyance air for conveying the fine particles, meaning that in such cases not only fine particles of tiny diameter but also particles whose diameter is large are conveyed, making difficult the conveying of only fine particles that are tiny to a level that can give rise to Brownian motion.

Generating/conveying only tiny fine particles necessitates controlling with high precision the voltage applied to the vibration elements and the rpm of the delivery machine at the same time, which without specialized knowledge is challenging.

In particular, selectively producing fine particles of tiny particle diameter requires lowering the rpm of the blower. Lowering the rpm of the blower enables making it so that air drafts are lowered, and large, heavy particles are not conveyed, therefore making it possible to selectively convey fine particles of tiny particle diameter. If, however, the rpm of the blower is lowered, because the fanning volume goes down at the same time, spraying across wide areas is impossible, making the spraying of assembly halls, livestock sheds, etc. challenging.

An object of the present invention, taking these sorts of issues into consideration, is to make available a spraying apparatus that, even for persons for whom the job is unfamiliar, is capable of generating a large volume of fine particles having particle diameters minute to a level that stably can give rise to Brownian motion, even without complex control employing expensive control devices.

Means for Resolving Issues

The present invention makes available the following sort of resolution means.

The invention involving a first characteristic makes available a spraying apparatus comprising: an atomization unit furnished with an atomization tank enabled for storing a liquid formulation, an atomizing device for atomizing the liquid formulation in the atomization tank interior to generate fine particles, and a blower furnished with a blowing element enabled for maintaining predetermined rpm, for blasting into the atomization tank interior, through a blow port provided in the atomization tank, conveyance air that is for conveying the fine particles of the liquid formulation; a tank unit for supplying the liquid formulation to the atomization tank; a spouting unit for spouting out together with conveyance air the fine particles generated in the atomization unit; and a mounting unit for fixing the atomization unit, the tank unit and the spouting unit; the spraying apparatus being wherein the mounting unit is furnished with a lower-part base located in the lower-end section, a plurality of columnar members fixed to the lower-part base and arranged directed upward, and a top component fixed to the upper ends of the columnar members; and the atomization tank is fixed to the lower-part base and meanwhile, above the atomization tank the tank unit is fixed to the columnar members, and the spouting unit is arranged on the top component.

According to the invention involving the first characteristic, by the atomization tank being anchored to the lower-part base, fine particles are produced in the lowest part of the spraying apparatus. What is more, by the spouting unit being disposed on the uppermost part upward of the tank unit arranged above the atomization tank, the fine particles that are produced ascend from the bottommost part of the apparatus and spout out from the uppermost part. Therefore afforded is a spraying apparatus 1 exploiting the chimney effect to enable the spraying of fine particles over a wide range, even in instances in which the rpm of the blowing element is lowered, lowering the pressure of the blower.

Appended Text 8

A spraying device 1 of Appended Text 8 is as follows.

TECHNICAL FIELD

The present invention relates to technology for generating fine particles in a spraying device that sprays liquid into a space.

BACKGROUND ART

Various spraying devices that atomize and spray into a space water or aqueous solutions that exhibit predetermined effects have been developed.

In spraying devices of this kind, in order to uniformly and wide-rangingly diffuse fine particles inside a space, it is necessary to stably generate fine particles having a desired particle size—in particular, a particle size tiny to a level at which the fine particles can give rise to Brownian motion within air.

As an example of this sort of spraying device, there is the instance in which, e.g., in a broad space such as an elderly-facility assembly hall, or livestock shelter such as a cow-shed, piggery, or poultry farm, the need arises to spray a large volume of a liquid formulation having a disinfecting action. In such instances, it is undesirable that the particle diameters be large, because the particles will fall to the floor or ground before reaching every nook and cranny of the space, and at the same time dampen the floor, walls, and skin, becoming the cause of slipping, of mold and mildew, and of colds. Therefore, in order that the particles float within the air for a long time such that the sterilizing effectiveness is demonstrated, it is necessary to generate fine particles having particle diameters tiny to a level that can give rise to Brownian motion.

In general, in order to atomize and spray a liquid, in an atomization unit in which water or an aqueous solution is stored, technology is adopted in which a liquid column generated utilizing a vibrator such as an ultrasonic vibrator is collided against a separator and separated into large liquid droplets and small mist droplets, and a conveyance medium supplied from a blower or the like is utilized to convey and diffuse into the air the mist droplets alone. (JP H8-309248 A, JP S60-50728 U)

SUMMARY OF INVENTION

Issues Invention Is to Address

The technology disclosed in JP H8-309248 A and JP S60-50728 U affords a spray apparatus capable of selectively spraying mist droplets separated from liquid droplets. Nevertheless, with the technology disclosed in JP H8-309248 A and JP S60-50728 U, because air is directly supplied to the region where the liquid column collides on the separator, due to the air the flow is disturbed, such that particles of relatively large particle diameter also get swept into and are conveyed on the air. Consequently, the particle diameter of fine particles conveyed on the air and sprayed is on the order of 10 μm, encumbering the generating of fine particles (particle size of about 0.1 to 2 μm) that are tiny to a level that can give rise to Brownian motion.

What is more, in order to carry out operational running that spreads fine particles evenly over a broad space, in the first place, it is necessary that start-up of the spray apparatus takes place swiftly, wherein when the spraying apparatus is being started up, the liquid formulation must be supplied swiftly into the atomization tank furnished with the ultrasonic vibration elements. On that occasion, going to the fuss of directly supplying the liquid formulation to the atomization tank takes time and effort. For this reason, a problem has been that while some apparatuses are furnished with a sub-tank, unless the sub-tank can be efficiently replenished with liquid formulation the spraying apparatus proves to have poor handling.

An object of the present invention, brought about taking these sorts of issues into consideration, is to make available, in spraying apparatuses capable of generating a large volume of fine particles having particle diameters minute to a level that can stably give rise to Brownian motion, a spraying apparatus with which replenishing liquid formulation to atomization tank can be carried out swiftly, and that is capable of spraying over a long period of time a large volume of liquid formulation stably over a broad range.

Means for Resolving Issues

The present invention makes available the following sort of resolution means.

The invention involving the first characteristic comprises an atomization tank enabled for storing a liquid formulation; an atomization device that atomizes the liquid formulation in the atomization tank to produce fine particles, and conveyance air that carries the fine particles of the liquid formulation. an atomizing unit including an air blower that produces an atomizing unit; a tank unit that is disposed above the atomization tank and supplies liquid to the atomization tank; a spouting unit that blows fine particles produced by the atomizing unit together with conveyance air; A top member is provided above the tank unit, and the top member has a top panel on which the spouting unit is installed, a top panel recess formed downward from the top panel, and an opening and closing that covers the top panel recess. and a liquid formulation replenishing port communicating with a tank unit is formed in a concave portion on the top panel.

According to the invention involving the first characteristic, that fact that the liquid formulation replenishing port for replenishing the tank unit with liquid formulation is furnished in the recess provided in the top panel of the top component means that replenishing-supply of liquid formulation from above in a high position in the apparatus is possible, which facilitates replenishing-supply of the liquid formulation. Further, because the liquid-formulation supply port is covered by the door-lid during the spraying operation, there is no danger of foreign matter entering into the tank unit interior, affording, moreover, a spraying apparatus with a neat appearance.

Appended Text 9

A spraying device 1 of Appended Text 9 is as follows.

TECHNICAL FIELD

The present invention relates to technology for generating fine particles in a spraying device that sprays liquid into a space.

BACKGROUND ART

Various spraying devices that atomize and spray into a space water or aqueous solutions that exhibit predetermined effects have been developed.

In spraying devices of this kind, in order to uniformly and wide-rangingly diffuse fine particles inside a space, it is necessary to stably generate fine particles having a desired particle size—in particular, a particle size tiny to a level at which the fine particles can give rise to Brownian motion within air.

As an example of this sort of spraying device, there is the instance in which, e.g., in a broad space such as an elderly-facility assembly hall, or livestock shelter such as a cow-shed, piggery, or poultry farm, the need arises to spray a large volume of a liquid formulation having a disinfecting action. In such instances, it is undesirable that the particle diameters be large, because the particles will fall to the floor or ground before reaching every nook and cranny of the space, and at the same time dampen the floor, walls, and skin, becoming the cause of slipping, of mold and mildew, and of colds. Therefore, in order that the particles float within the air for a long time such that the sterilizing effectiveness is demonstrated, it is necessary to generate fine particles having particle diameters tiny to a level that can give rise to Brownian motion.

In general, in order to atomize and spray a liquid, in an atomization unit in which water or an aqueous solution is stored, technology is adopted in which a liquid column generated utilizing a vibrator such as an ultrasonic vibrator is collided against a separator and separated into large liquid droplets and small mist droplets, and a conveyance medium supplied from a blower or the like is utilized to convey and diffuse into the air the mist droplets alone. (JP H8-309248 A, JP S60-50728 U)

SUMMARY OF INVENTION

Issues Invention is to Address

The technology disclosed in JP H8-309248 A and JP S60-50728 U affords a spray apparatus capable of selectively spraying mist droplets separated from liquid droplets. Nevertheless, with the technology disclosed in JP H8-309248 A and JP S60-50728 U, because air is directly supplied to the region where the liquid column collides on the separator, due to the air the flow is disturbed, such that particles of relatively large particle diameter also get swept into and are conveyed on the air. Consequently, the particle diameter of fine particles conveyed on the air and sprayed is on the order of 10 μm, encumbering the generating of fine particles (particle size of about 0.1 to 2 μm) that are tiny to a level that can give rise to Brownian motion.

What is more, considering that the apparatus will be set up in variety of places, preferably the apparatus itself is not made to have protrusions or the like, giving it a sleek design. Still further, even in implementations scaled-up giving consideration to spraying large volumes of fine particles, it is desirable to make it so that even persons unused to the work can remove the surrounding cover and check the interior without an expert lending a hand.

An object of the present invention, brought about taking these sorts of issues into consideration, is to make available a spraying apparatus of advanced design qualities that even in implementations in which the apparatus has been scaled up for the sake of large-volume liquid formulation spraying over wide areas, enables even persons unfamiliar with the work to readily take off and put on the cover, and that at the same time, no matter where it is set up it can be installed without a sense of incongruity.

Means for Resolving Issues

The present invention makes available the following sort of resolution means.

The invention involving a first characteristic makes available a spraying apparatus comprising: an atomization unit furnished with an atomization tank enabled for storing a liquid formulation, an atomizing device for atomizing the liquid formulation in the atomization tank interior to generate fine particles, and a blower for producing conveyance air that carries the fine particles of the liquid formulation; a tank unit arranged above the atomization unit, for supplying liquid formulation to the atomization tank; a spouting unit for spouting out together with the conveyance air the fine particles generated in the atomization unit; and a mounting unit for fixing the atomization unit and the tank unit, and a cover member for covering the atomization unit, the tank unit and the mounting unit; the spraying apparatus being wherein the mounting unit is furnished with a lower-part base located in the lower-end section, and a plurality of columnar members fixed to the lower-part base and arranged directed upward, and the cover member is formed of a stainless-steel sheet having elasticity, and arranged on the periphery of the plurality of columnar members so as to cover the mounting unit.

According to the invention involving the first characteristic, the fact that the periphery of the columnar members is covered with the cover member formed by a stainless-steel sheet affords a spraying apparatus that enables the atomization unit, the tank unit, etc. to be covered and concealed from the external environment, and that at the same time gives a sleek impression. In addition, since the cover member is formed by a sheetlike component having elasticity, it can be arranged utilizing the elastic force to wrap it onto the periphery of the columnar members, so that even persons unused to the job can easily attach and detach the cover member. Furthermore, the fact that the cover member is strong against corrosion by acids, affords a spraying apparatus that enables the utilization of various liquid formulations, and that can be employed in various environments.

Appended Text 10

A decontaminating apparatus 1 of Appended Text 10 is as follows.

TECHNICAL FIELD

The present invention relates to technology for generating fine particles in a decontaminating apparatus for spraying into a space a liquid having decontaminating action.

BACKGROUND ART

Various decontaminating apparatuses that atomize a liquid having decontaminating action and spray it into a space have been developed.

In decontaminating apparatuses of this kind, in order to uniformly and wide-rangingly diffuse fine particles inside a space, it is necessary to stably generate fine particles having a desired particle size—in particular, a particle size tiny to a level at which the fine particles can give rise to Brownian motion within air.

As an example of this sort of decontaminating apparatus, there is the instance in which, e.g., in a broad space such as an elderly-facility assembly hall, or livestock shelter such as a cowshed, piggery, or poultry farm, the need arises to spray a large volume of a liquid formulation having a disinfecting action. In such instances, it is undesirable that the particle diameters be large, because the particles will fall to the floor or ground before reaching every nook and cranny of the space, and at the same time dampen the floor, walls, and skin, becoming the cause of slipping, of mold and mildew, and of colds. Therefore, in order that the particles float within the air for a long time such that the sterilizing effectiveness is demonstrated, it is necessary to generate fine particles having particle diameters tiny to a level that can give rise to Brownian motion.

In general, in order to atomize and spray a liquid, in an atomization unit in which water or an aqueous solution is stored, technology is adopted in which a liquid column generated utilizing a vibrator such as an ultrasonic vibrator is collided against a separator and separated into large liquid droplets and small mist droplets, and a conveyance medium supplied from a blower or the like is utilized to convey and diffuse into the air the mist droplets alone. (JP H8-309248 A, JP S60-50728 U)

SUMMARY OF INVENTION

Issues Invention Is to Address

The technology disclosed in JP H8-309248 A and JP S60-50728 U affords a spray apparatus capable of selectively spraying mist droplets separated from liquid droplets. Nevertheless, with the technology disclosed in JP H8-309248 A and JP S60-50728 U, because air is directly supplied to the region where the liquid column collides on the separator, due to the air the flow is disturbed, such that particles of relatively large particle diameter also get swept into and are conveyed on the air. Consequently, the particle diameter of fine particles conveyed on the air and sprayed is on the order of 10 µm, encumbering the generating of fine particles (particle size of about 0.1 to 2 µm) that are tiny to a level that can give rise to Brownian motion.

What is more, when spraying particles having a decontaminating action, the liquid formulation employed is generally an aqueous sodium hypochlorite solution. With sodium hypochlorite aqueous solutions, given that minute particles such as described above are prone to becoming deactivated, it producing particles tiny to a level that can give rise to Brownian motion has been challenging.

Furthermore, liquid formulations with a decontaminating action are generally acidic, which leads to problems including corrosion of the components constituting the apparatus.

An object of the present invention, brought about taking these sorts of issues into consideration, is to make available a decontaminating apparatus that without employing an aqueous sodium hypochlorite solution enables the large-volume generating of fine particles having particle diameters minute to a level that can stably give rise to Brownian motion, and that is not susceptible to corrosion occurring and is capable of running stably over a long period of time.

Means for Resolving Issues

The present invention makes available the following sort of resolution means.

The invention involving the first characteristic comprises an atomization tank capable of storing an aqueous solution of chlorous acid as a liquid formulation, an atomization device for atomizing the liquid formulation in the atomization tank to generate fine particles, and fine particles of the liquid formulation. an atomizing unit including a blower that discharges conveyance air into the atomization tank from a blow port provided in the atomization tank, a tank unit that supplies the liquid formulation to the atomization tank, and an atomizing unit and an mounting unit for fixing the atomizing unit, the tank unit and the spouting unit, wherein the atomization tank and the tank unit are made of polyethylene terephthalate. As formed, the mounting unit provides a sterilization device, formed by stainless steel.

According to the invention involving the first characteristic, by atomizing the chlorous acid aqueous solution utilizing ultrasonic vibration elements, fine particles tiny to a level that can give rise to Brownian motion can be generated. In addition, because the fine particles generated utilizing the chlorous acid aqueous solution are not prone to becoming deactivated even after a long-term elapse of time, the decontaminating effect can continue over a long period of time. In that situation, the fact that the atomization tank and the tank unit are formed from polyethylene terephthalate, which possesses strong properties against chlorous acid, affords a decontaminating apparatus that does not require carrying out long-term maintenance, and that is capable of being run continuously. Likewise, because the mounting unit is made of stainless steel, it is not susceptible to corrosion, and the component replacement and the like that is attendant on rusting can be avoided, enabling stabilized running over still longer periods of time.

EXPLANATION OF REFERENCE MARKS

1 Sprayer
10 Atomizing unit
  11 Atomization tank
    11*a* Inlet
    11*b* Blow port
    11*c* Send-out port
    11*d* Top panel
  12 Atomization device
    12*a, b* . . . Ultrasonic vibration elements
  13 Blower
  14*a, b* Baffle plate
  15 Liquid-level sensor
  16 Halt sensor
20 Tank unit
30 Spouting unit
  31 Spouting element
  32 Spray port
40 Supply unit
50 Control unit
60 Mounting unit
  61 Lower-part base
  62 Columnar member
  63 Top member
  64 Legs
70 Power supply unit
80 Cover member

The invention claimed is:

1. A spraying apparatus comprising:

an atomization tank having a predetermined width, enabled for storing a liquid formulation;

an atomizing device being ultrasound vibrating elements plurally arranged widthwise in the atomization tank interior, for atomizing the liquid formulation to generate fine particles;

a blower furnished with a blowing element enabled for maintaining predetermined rpm, for blasting into the atomization tank interior, through a blow port provided in the atomization tank, conveyance air that is for conveying the fine particles of the liquid formulation;

a send-out port, provided in the atomization tank, through which the fine particles are sent out together with the conveyance air;

a first baffle plate arranged so as to receive liquid columns of the liquid formulation, produced by an ultrasound vibration element that among said ultrasound vibration elements is arranged along one widthwise end thereof;

a second baffle plate arranged so as to receive liquid columns of the liquid formulation, produced by an ultrasound vibration element that among said ultrasound vibration elements is arranged along the other widthwise end thereof; wherein the first baffle plate is arranged inclined laterally or diagonally downward, directed toward the one widthwise end of the atomization tank, and is furnished with a first edge part disposed in the atomization tank spaced apart at a predetermined spacing from an inner face along the one widthwise end, and with a first connection part, connected to an inner side of a top panel of the atomization tank;

the blow port is arranged along the top panel of the atomization tank more to the one widthwise end of the atomization tank than is the first connection part, and more to the other widthwise end of the atomization tank than is the first edge part;

the second baffle plate is arranged inclined laterally or diagonally downward, directed toward the other widthwise end of the atomization tank, and is furnished with a second edge part disposed in the atomization tank spaced apart at a predetermined spacing from an inner face along the other widthwise end, and with a second connection part, connected to the inner side of the top panel of the atomization tank; and the send-out port is arranged more toward the other widthwise end of the atomization tank than is the second connection part.

2. The spraying apparatus set forth in claim 1, further provided with a control unit for controlling the rpm of the blowing element.

3. A spraying apparatus comprising:

an atomization tank having a predetermined width, enabled for storing a liquid formulation;

an atomizing device being ultrasound vibrating elements plurally arranged widthwise in the atomization tank interior, for atomizing the liquid formulation to generate fine particles;

a blower furnished with a blowing element enabled for maintaining predetermined rpm, for blasting into the atomization tank interior, through a blow port provided in the atomization tank, conveyance air that is for conveying the fine particles of the liquid formulation;

a send-out port, provided in the atomization tank, through which the fine particles are sent out together with the conveyance air;

a first baffle plate arranged so as to receive liquid columns of the liquid formulation, generated produced by an ultrasound vibration element that among said ultrasound vibration elements is arranged along one widthwise end thereof;

a second baffle plate arranged so as to receive liquid columns of the liquid formulation, produced by an ultrasound vibration element that among said ultrasound vibration elements is arranged along the other widthwise end thereof; wherein the first baffle plate is arranged inclined laterally or diagonally downward, directed toward the one widthwise end of the atomization tank, and is furnished with a first edge part disposed in the atomization tank spaced apart at a predetermined spacing from an inner face along the one widthwise end, and with a first connection part, connected to an inner side of a top panel of the atomization tank;

the blow port is arranged in a lateral surface along the one widthwise end of the atomization tank, upward of the first edge part;

the second baffle plate is arranged inclined laterally or diagonally downward, directed toward the other widthwise end of the atomization tank, and is furnished with a second edge part disposed in the atomization tank spaced apart at a predetermined spacing from an inner face along the other widthwise end, and with a second connection part, connected to the inner side of the top panel of the atomization tank with; and the send-out port is arranged more toward the other widthwise end of the atomization tank than is the second connection part.

4. The spraying apparatus set forth in claim 3, further provided with a control unit for controlling the rpm of the blowing element.

* * * * *